(12) United States Patent
Hirata et al.

(10) Patent No.: US 6,265,495 B1
(45) Date of Patent: Jul. 24, 2001

(54) METHOD FOR PRODUCTION OF ESTERIFIED PRODUCT

(75) Inventors: Tsuyoshi Hirata, Kobe; Tsutomu Yuasa, Osaka, both of (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/399,491

(22) Filed: Sep. 20, 1999

(30) Foreign Application Priority Data

Sep. 22, 1998 (JP) .................................................. 10-268122
Nov. 18, 1998 (JP) .................................................. 10-328687

(51) Int. Cl.$^7$ .............................. C08F 2/40; C08F 283/06
(52) U.S. Cl. ........................ 525/404; 106/819; 525/451; 526/932; 560/189; 560/224
(58) Field of Search .................................... 525/404, 451; 523/436; 526/932; 106/819; 560/224, 189

(56) References Cited

U.S. PATENT DOCUMENTS

| | | | |
|---|---|---|---|
| 2,815,369 | * 12/1957 | Holt | 560/224 |
| 3,708,445 | * 1/1973 | Junas et al. | 526/932 X |
| 3,896,161 | * 7/1975 | Borden et al. | 560/224 |
| 4,138,381 | * 2/1979 | Chang et al. | 526/932 X |
| 4,268,641 | * 5/1981 | Koenig et al. | 526/932 X |
| 4,528,334 | * 7/1985 | Knopf et al. | 525/404 |
| 4,774,178 | 9/1988 | Egerer et al. | 435/41 |
| 4,933,428 | * 6/1990 | Piepho et al. | 525/451 X |
| 5,362,324 | * 11/1994 | Cerulli et al. | 106/819 X |
| 5,539,064 | * 7/1996 | Hashimoto et al. | 525/404 X |
| 5,780,546 | * 7/1998 | Pugach et al. | 525/451 X |
| 5,952,432 | * 9/1999 | Yamaguchi et al. | 525/404 |

FOREIGN PATENT DOCUMENTS

| | | |
|---|---|---|
| 0799807A2 | 4/1997 | (EP) . |
| 0884290A2 | 6/1998 | (EP) . |
| 59-18338 | 4/1984 | (JP) . |
| 59-67244 | 4/1984 | (JP) ................................ C07C/69/54 |
| 59-108741 | 6/1984 | (JP) ................................ C07C/69/54 |
| 59-141576 | 8/1984 | (JP) ................................ C07D/317/24 |
| 63-122649 | 5/1988 | (JP) ................................ C07C/69/54 |
| 7-224004 | 2/1994 | (JP) . |
| 10-153599 | 11/1996 | (JP) . |
| 09-86990 | 3/1997 | (JP) . |
| 09-286645 | 11/1997 | (JP) . |
| 10-53599 | 2/1998 | (JP) ................................ C07C/69/54 |

* cited by examiner

Primary Examiner—Richard D. Lovering
(74) Attorney, Agent, or Firm—Mathews, Collins Shepherd & Gould P.A.

(57) ABSTRACT

A method for the production of an esterified product is provided which affords an esterified product with high quality by repressing, during the esterification reaction of an alcohol with (meth)acrylic acid, the occurrence of impurities, particularly gel, to be formed owing to the polymerization of the alcohol and the (meth)acrylic acid as raw materials, the esterified product consequently formed, or the mixture thereof. Specifically, a method for the production of an esterified product of this invention comprises esterifying an alcohol represented by the following formula (1):

$$R^1O(R^2O)_nH \qquad (1)$$

wherein $R^1$ represents a hydrocarbon group of 1 to 30 carbon atoms, $R^2O$ represents an oxyalkylene group of 2 to 18 carbon atoms, providing that the repeating units, $R^2O$, may be the same or different and that when the $R^2O$'s are in the form of a mixture of two or more species, the repeating units, $R^2O$, may be added either in a block form or in a random form, and n represents an average addition mol number of oxyalkylene groups and is in the range of 0 to 300, with (meth)acrylic acid in a dehydrating solvent in the presence of an acid catalyst and a polymerization inhibitor, wherein a reaction temperature during the esterification reaction is not higher than 130° C. and a circulation speed of the solvent during the esterification reaction is not less than 0.5 cycle/hour.

9 Claims, 3 Drawing Sheets

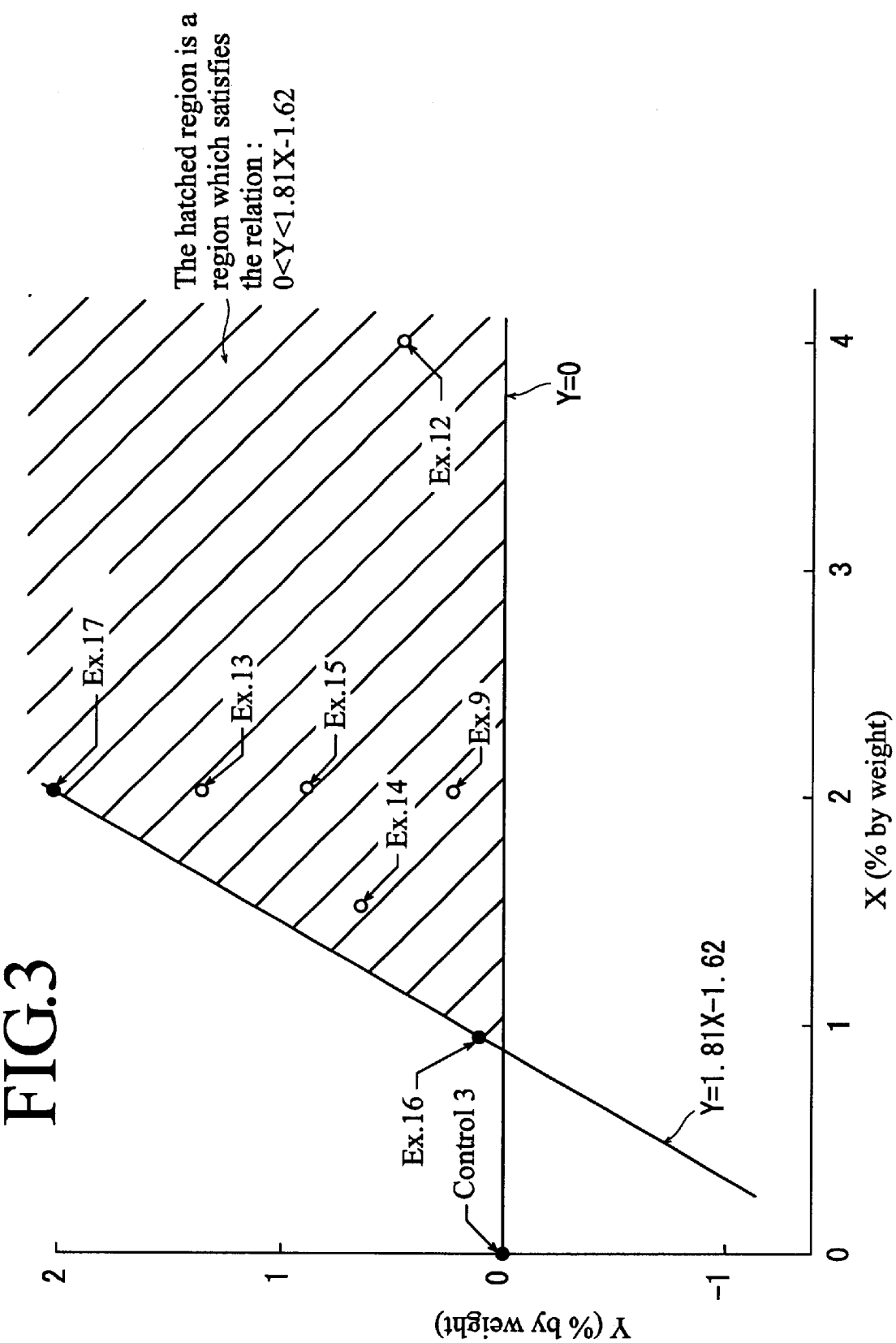

METHOD FOR PRODUCTION OF ESTERIFIED PRODUCT

BACKGROUND OF THE INVENTION

1. Field of the Invention

This invention relates to a method for the production of an esterified product. More particularly, this invention relates to a method for the production of an esterified product of high quality, in the production of the esterified product by the esterification reaction of an alcohol with (meth)acrylic acid in a dehydrating solvent in the presence of an acid catalyst and a polymerization inhibitor.

Further, this invention relates to a method for the production of an alkoxy polyalkylene glycol mono(meth)acrylic acid type monomer for the use in a cement dispersant, and to a cement dispersant containing a polycarboxylic acid type copolymer using the monomer obtained by the method. More particularly, this invention relates to a method for the production of an alkoxy polyalkylene glycol mono(meth)acrylic acid type monomer which is capable of repressing the formation of impurities, particularly gel, liable to degrade the cement-dispersing ability by producing the alkoxy polyalkylene glycol mono(meth)acrylic acid type monomer by the esterification reaction of a polyalkylene glycol with (meth)acrylic acid in a dehydrating solvent in the presence of an acid catalyst and a polymerization inhibitor and which method is excellent in productivity (as evinced by a short reaction time and an outstanding reaction velocity), and to a cement dispersant containing a polycarboxylic acid type copolymer using a monomer obtained by the method mentioned above.

2. Description of the Related Art

Since the early deterioration of concrete structures became an object of social concern in 1981, the desirability of decreasing an unit water content in concrete and exalting durability and workability of concrete has been finding hearty approval. The development of a cement composition fulfilling this demand as well as the development of a cement dispersant which has a profound influence on the quality and performance of the cement composition has been promoted vigorously. The polymer component which is used in the cement dispersant, in pigment dispersants for calcium carbonate, carbon black, ink, and other pigments, and in scale removers, dispersants for a slurry of gypsum and water, dispersants for CWM, thickeners, and etc. is obtained by using a varying (meth)acrylic ester (occasionally referred to simply as "esterified product" in the present specification) to be obtained by the esterification of an alcohol with (meth)acrylic acid as a monomer component and polymerizing the monomer component.

It has been known that in this esterification, the alcohol and (meth)acrylic acid as the raw materials, the esterified product, or the mixture thereof are fated to be polymerized and form a gel. It is, therefore, usual to perform this esterification with a suitable polymerization inhibitor incorporated in the monomer mixture with a view to preventing this polymerization.

Among other inventions relating to the esterification reactions, JP-A-09-328,346 discloses a cement dispersant which contains a polymer (A) derived by using an alkoxy polyalkylene glycol (meth)acrylic ester type monomer obtained by subjecting an alkoxy polyalkylene glycol and a (meth)acrylic ester to the reaction of interesterification in the presence of a basic catalyst, a (meth)acrylic acid (salt) type monomer, and a monomer copolymerizable with such monomers and/or a polymer salt (B) obtained by further neutralizing the polymer (A) with an alkaline substance. Controls 1 and 2 cited in the patent publication mentioned above, as concrete examples of performing the esterification reaction in the presence of an acid catalyst, describe an operation of installing a reaction vessel provided with a reactor (a separable flask) incorporating therein a thermometer, a stirrer, and a water separating device and adapted to effect separation of the water formed by the reaction, charging the reaction vessel with methacrylic acid, methoxypolyethylene glycol (the average addition mol number of oxyethylene groups : 10 mols), sulfuric acid (Control 1) or paratoluene sulfonic acid (Control 2) as an acid catalyst, phenothiazine as a polymerization inhibitor, and cyclohexane as a dehydrating solvent, stirring and meanwhile heating the reactants therein to effect esterification and, at the same time, induce distillation of a cyclohexane-water azeotrope under normal pressure, removing water formed by the reaction with the water separating device and meanwhile refluxing cyclohexane.

The patent publication mentioned above, however, discloses that when the esterification is carried out in the presence of an acid catalyst, the acid catalyst is deficient in water-reducing properties as compared with a base catalyst and the esterification by the use of the acid catalyst by-produces (poly)alkylene glycol having hydroxyl groups at both terminals in consequence of ether cleavage of the alkoxy polyalkylene glycol, which by-product undergoes the esterification reaction with (meth)acrylic acid to give rise to a bifunctional di(meth)acrylic ester type monomer, and this monomer further acts as a cross-linking agent in the subsequent polymerization reaction and inevitably forms a cross-linked polymer having a high molecular weight and poor cement-dispersing properties. Specifically, in this patent publication, Table 1 showing the results of Controls 1 and 2 indicates that the relevant cross-linked components were formed in such large amounts respectively as of 12.0% and 14.6% during the reaction of the esterified products and that the esterification reactions both consumed long periods of 25 hours.

In addition to the drawback mentioned above, even the use of a proper polymerization inhibitor possibly results in forming a gel during the esterification as stated in the patent publication mentioned above. The occurrence of such gel proves extremely inconvenient in the case of mass production of a cement dispersant because of necessity of an extra process of separating the gel by filtration. To be specific, the operation of this production cannot be carried out continuously but must be stopped after each batch for the purpose of transferring the product into another device to separate by filtration the gel generated in the interior of the reaction vessel. Further, the part of the gel suffered to adhere to the inner wall of the reaction vessel is a mischievous entity liable to obstruct the continuous production because the inner wall must be washed to remove the gel and the work of this washing entails a needless addition to the number of production steps and requires to use a special device. As regards the fact that the gel occurs despite the use of an polymerization inhibitor, the patent publication mentioned above states that the esterification reaction, when carried out in the presence of an acid catalyst, by-produces (poly) alkylene glycol having hydroxyl groups at both terminals owing to ether cleavage of the alkoxy polyalkylene glycol as the raw material and suffers this by-product to undergo the esterification reaction with (meth)acrylic acid to give rise to a bifunctional di(meth)acrylic ester type monomer. No means of solving this problem, however, is disclosed anywhere in this patent publication. The esterification further has the problem that the polymer consequently obtained, when used in a proper application such as a cement dispersant, fails to manifest fully satisfactory cement-dispersing properties because the esterified product containing this di(meth)acrylic ester type monomer, on being polymerized, functions as a cross-linking agent and inevitably results in forming a cross-linked polymer having a high molecular weight and poor dispersing properties.

Regarding the method for esterifying in the presence of an acid catalyst, however, any means for repressing the formation of such impurities as mentioned above or any means for expediting the esterification reaction has never been reported to the literature.

SUMMARY OF THE INVENTION

An object of this invention, therefore, is to provide a method for the production of an esterified product which is capable of repressing the occurrence of impurities, particularly gel, possibly formed during the esterification reaction of an alcohol with (meth)acrylic acid in a dehydrating solvent in the presence of an acid catalyst and a polymerization inhibitor owing to the polymerization of the alcohol and the (meth)acrylic acid as raw materials, the esterified product consequently formed, or a mixture thereof and also capable of obtaining the product with high quality.

Another object of this invention is to provide a method for the production of an esterified product which represses the formation of gel in the esterification reaction of an alcohol with (meth)acrylic acid in a dehydrating solvent in the presence of an acid catalyst and a polymerization inhibitor and, as a result, obviates the necessity for using a step of removing the gel by filtration, and allows the esterified product to be mass-produced by a continuous operation on a commercial scale.

Still another object of this invention is to provide a method for the production of an esterified product which, by performing the esterification reaction mentioned above in a dehydrating solvent in the presence of an acid catalyst and a polymerization inhibitor, enables the esterified product to be produced quickly and efficiently with high quality.

Yet another object of this invention is to provide a method for the production of an esterified product which, by repressing the occurrence of impurities, particularly gel, in the esterification reaction of a polyalkylene glycol with (meth) acrylic acid in a dehydrating solvent in the presence of an acid catalyst and a polymerization inhibitor, can manifest excellent properties suitable for various applications and find utility as a monomer component of a polymer to be used particularly in a cement dispersant having outstanding cement-dispersing properties, and also a cement dispersant containing the polymer using the monomer component and excelling in performance.

The present inventors, for the fulfillment of the tasks mentioned above, have pursued a diligent study on methods for the production of esterified products by the esterification reaction of an alcohol with (meth)acrylic acid in a dehydrating solvent in the presence of an acid catalyst and a polymerization inhibitor. As a result, they have found that the impurities are increased and the cement-dispersing properties are degraded when the temperature of the esterification surpasses a prescribed level and further found that in the operation of causing the dehydrating solvent in the reaction system to be expelled by distillation during the esterification reaction, condensing and liquefying the expelled vapor, and circulating the condensate back to the reaction system, the reaction time is notably elongated when the circulation speed of the solvent is low. Based on the knowledge thus acquired, they have found a solution capable of repressing the formation of impurities and enabling the esterified product to be quickly and efficiently produced with high quality.

Besides the knowledge mentioned above, the present inventors have also found that when the esterification reaction is performed with the acid catalyst in the form of a hydrate and/or an aqueous solution, proper adjustment of the acid component and the water component in this acid catalyst realizes a condition for enabling the polymerization inhibitor to function very effectively and inducing repression of the formation of gel.

The present inventors have further found that the cement dispersant containing the polymer obtained by polymerizing the esterified product resulting from the aforementioned esterification reaction exhibits outstanding cement-dispersing properties. The present invention has been perfected on the basis of such knowledge.

Specifically, the objects of this invention can be accomplished by a method for the production of an esterified product which comprises esterifying an alcohol represented by the following formula (1) (occasionally referred to simply as "alcohol" in the present specification):

$$R^1O(R^2O)_nH \qquad (1)$$

wherein $R^1$ represents a hydrocarbon group of 1 to 30 carbon atoms, $R^2O$ represents an oxyalkylene group of 2 to 18 carbon atoms, providing that the repeating units, $R^2O$, may be the same or different and that when the $R^2O$'s are in the form of a mixture of two or more species, the repeating units, $R^2O$, may be added either in a block form or in a random form, and n represents an average addition mol number of oxyalkylene groups and is in the range of 0 to 300, with (meth)acrylic acid in a dehydrating solvent in the presence of an acid catalyst and a polymerization inhibitor, wherein a reaction temperature during the esterification reaction is not higher than 130° C. and a circulation speed of the solvent during the esterification reaction is not less than 0.5 cycle/hour.

The method of this invention for the production of the esterified product, by setting the reaction temperature during the esterification reaction at not higher than 130° C. and setting the circulation speed of the solvent during the esterification reaction at not less than 0.5 cycle/hour, can bring following advantages, i.e. the advantage that the cement dispersant synthesized by using the resultant esterified product veritably excels in cement-dispersing properties because this method is capable of precluding the formation of such harmful impurities as would persist in the reaction system up to the stage of finished product; and the advantage that the reaction time can be markedly shortened because the method effects thorough dehydration of the interior of the reaction system.

Then, the esterification reaction, by using the acid catalyst particularly in the form of a hydrate and/or an aqueous solution and also adjusting the amount of the acid catalyst to be used within a specific range, can repress the formation of gel during the course of the esterification reaction and give the esterified product with unusually high quality. Further, the esterified product is very useful as a monomer component for a polymer component which is capable of manifesting a fine performance in various applications such as, for example, a pigment dispersant for calcium carbonate, carbon black, ink, and other pigments, and a scale remover, a dispersant for a slurry of gypsum and water, a dispersant for CWM, a thickener, as well as a cement dispersant. That is, the method represses the formation of gel fated to generate a high-molecular weight cross-linked polymer having poor dispersing properties, a possible cause for adverse effects such as on the dispersing property which is the basic quality required for such applications as mentioned above and, consequently, enables the product thereof to manifest excellent dispersing properties. This method provided by the present invention is suitable for continuous mass-production of the esterified product on a commercial scale because it represses the formation of gel during the course of the esterification reaction and, consequently, finds no use for any separation step of gel by filtration.

This invention, by using the hydrate and/or the aqueous solution of paratoluene sulfonic acid as the acid catalyst, not only permits such function and effect as mentioned above to be manifested but also prevents the cleavage of alcohol as a raw material by the acid catalyst which constitutes itself one of the causes for the formation of gel liable to degrade the quality and performance of the esterified product from readily occurring, enables the catalytic action to be effectively manifested as required, and ensures the production of an esterified product with an unusually high quality.

In addition to the advantages mentioned above, when the polymerization inhibitor mentioned above to be used in the method of this invention is at least one member selected from the group consisting of phenothiazine, methoquinone, and hydroquinone, particularly phenothiazine and the acid catalyst is used in the form of a hydrate and/or an aqueous solution, the polymerization inhibitor is capable of not only functioning effectively on the gel-forming substance present in the aqueous solution in the reaction system but also manifesting, while the dehydrating solvent is expelled by azeotropic distillation with water after completion of the esterification reaction, the polymerization inhibiting property quite effectively without any recourse to such a water-soluble polymerization inhibitor as methoquinone or hydroquione which exhibits a polymerizing activity, though only feebly. Thus, the method is highly useful from the viewpoint of being capable of effectively repressing the formation of high-molecular-weight products.

The above and other objects, features, and advantages of the present invention will become clear from the following description of the preferred embodiments.

BRIEF DESCRIPTION OF THE DRAWINGS

FIG. 3 is an X–Y correlation diagram obtained by plotting the (X, Y) coordinates formed in Example 9 and Examples 12 to 17 and Control 3, additionally showing a relational expressions of Y=1.81X−1.62 and Y=0.

DESCRIPTION OF THE PREFERRED EMBODIMENTS

Figure 1:
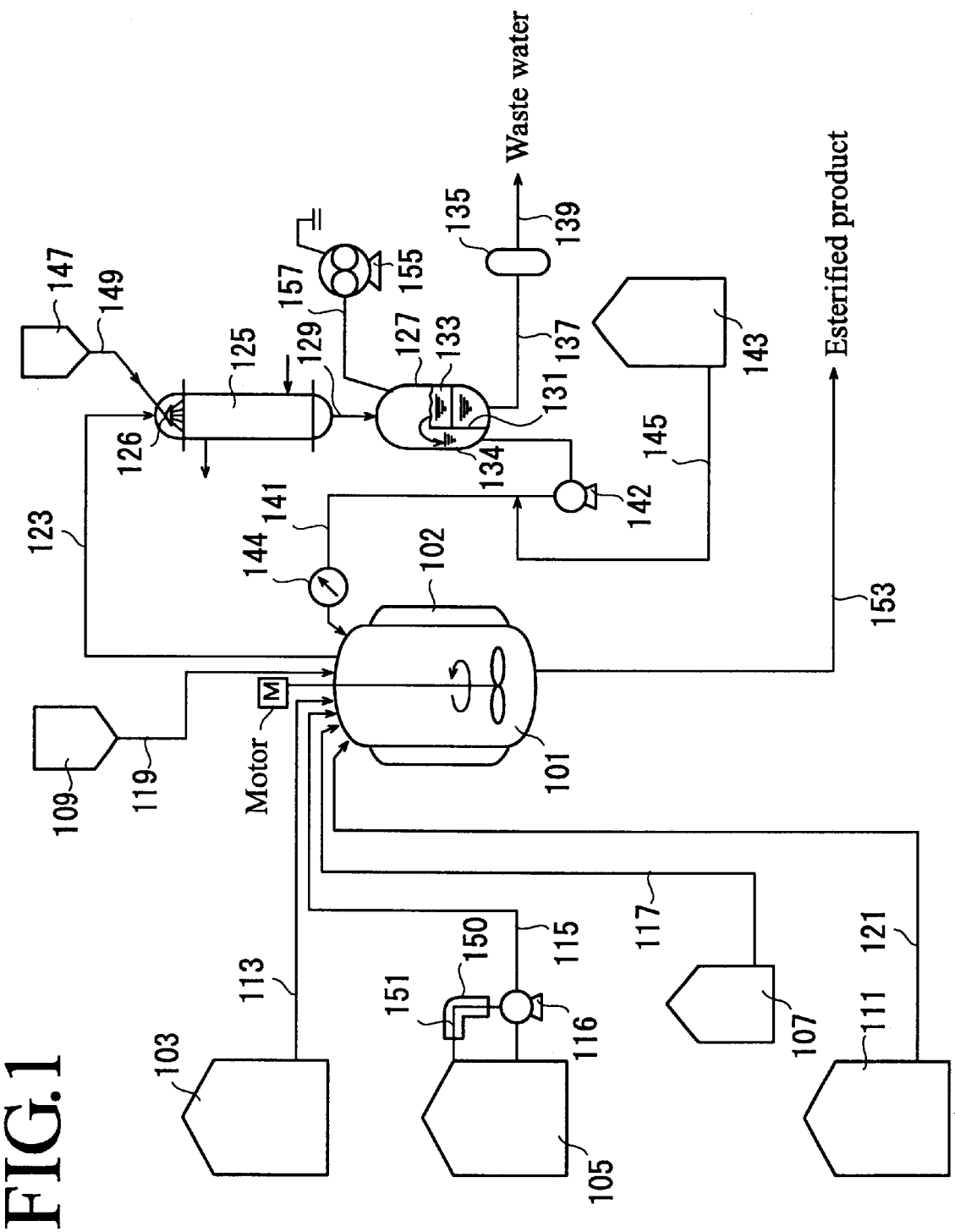
FIG. 1 is a schematic diagram illustrating the construction of a typical apparatus to be used in the method of this invention for the production of an esterified product.

Now, this invention will be described in detail below.

According to the first aspect, this invention provides a method for the production of an esterified product which comprises esterifying an alcohol represented by the following formula (1):

$$R^1O(R^2O)_nH \tag{1}$$

wherein $R^1$ represents a hydrocarbon group of 1 to 30 carbon atoms, $R^2O$ represents an oxyalkylene group of 2 to 18 carbon atoms, providing that the repeating units, $R^2O$, may be the same or different and that when the $R^2O$'s are in the form of a mixture of two or more species, the repeating units, $R^2O$, may be added either in a block form or in a random form, and n represents an average addition mol number of oxyalkylene groups and is in the range of 0 to 300, with (meth)acrylic acid in a dehydrating solvent in the presence of an acid catalyst and a polymerization inhibitor, wherein a reaction temperature during the esterification reaction is not higher than 130° C. and a circulation speed of the solvent during the esterification reaction is not less than 0.5 cycle/hour.

An alcohol which may be used as a raw material in the esterification reaction according to this invention is a compound of the above formula (1).

In the formula (1) mentioned above, $R^1$ represents a hydrocarbon group of 1 to 30 carbon atoms. If $R^1$ represents a hydrocarbon group having more than 30 carbon atoms, a copolymer obtained by copolymerizing the esterified product between the alcohol of the formula (1) and (meth)acrylic acid with (meth)acrylic acid, for example, will suffer degradation of water solubility and degradation of service performance such as, for example, cement-dispersing properties. The proper range of $R^1$ varies with the kind of intended use of the product. When the product is used as a raw material for a cement dispersant, for example, $R^1$ may preferably stand for a straight or branched-chain alkyl or aryl group of 1 to 18 carbon atoms. As concrete examples of $R^1$, alkyl groups such as methyl, ethyl, n-propyl, isopropyl, n-butyl, tert-butyl, pentyl, hexyl, octyl, nonyl, 2-ethylhexyl, decyl, dodecyl, undecyl, tridecyl, tetradecyl, pentadecyl, hexadecyl, heptadecyl, octadecyl, nonadecyl, eicocyl, heneicocyl, and dococyl; aryl groups such as phenyl; alkylphenyl groups such as benzyl and nonylphenyl; cycloalkyl groups such as cyclohexyl; and alkenyl groups and alkinyl groups may be cited. When the esterified product is used as a raw material for a cement dispersant, methyl, ethyl, propyl, butyl, and phenyl may be particularly favorable among other groups mentioned above.

$R^2O$ represents an oxyalkylene group of 2 to 18 carbon atoms, preferably 2 to 8 carbon atoms. If $R^2O$ represents an oxyalkylene group of more than 18 carbon atoms, a copolymer obtained by copolymerizing the esterified product between the alcohol of the formula (1) and (meth)acrylic acid with (meth)acrylic acid, for example, will suffer degradation of water solubility and degradation of service performance such as, for example, cement-dispersing properties. As concrete examples of $R^2O$, oxyethylene, oxypropylene, oxybutylene, and oxystyrene may be cited. Of these groups, oxyethylene, oxypropylene, and oxybutylene may prove favorable. The repeating units, $R^2O$, may be either the same or different. When the repeating units, $R^2O$, are variable, namely when the repeating units occur in not less than two species, these individual repeating units, $R^2O$, may be added in a block form or in a random form.

In the formula (1), n denotes a numeral falling in the range of 0 to 300, preferably 2 to 300, and represents an average addition mol number of the repeating units, $R^2O$ (oxyalkylene group). If n exceeds 300, the esterified product between the compound of the formula (1) and (meth)acrylic acid will suffer a degraded polymerizing properties. This average addition mol number, n, has the optimum range thereof varying with the purpose for which the esterified product obtained by the esterification reaction is used. When the esterified product is used as a raw material for a cement dispersant, for example, the average addition mol number, n, may be preferably in the range of 2 to 300, more preferably in the range of 5 to 200, and most preferably in the range of 8 to 150. When it is used in a thickener, the average addition mol number, n, may be preferably in the range of 10 to 250, more preferably in the range of 50 to 200. When n is 0, the aforementioned $R^1$ may be preferably a hydrocarbon group of not less than four carbon atoms from the viewpoint of solubility in water and boiling point. The reason for thus specifying the $R^1$ is that when n in the formula (1) is 0, particularly in the case of methanol or ethanol, the alcohol as the raw material is partially expelled by distillation out of the system and the esterified product aimed at is obtained in an unduly low yield because these alcohols, on account of a low boiling point, is vaporized together with water formed by the reaction and further dissolved in water.

In the method of this invention, the alcohol as the raw material of the aforementioned formula (1) may be used either singly or in the form of a mixture of two or more species. The mode of using the raw material alcohol in the form of a mixture of two or more species does not need to be limited particularly. The mixture of not less than two species having at least one of the factors, $R^1$, $R^2O$, and n varied may suffice as the mode of use. As concrete examples of the mode of preferable use, the case in which $R^1$ is composed of the two species, methyl and butyl; the case in which $R^2O$ is composed of the two species, oxyethylene and oxypropylene; the case in which n is composed of two species, one of 1 to 10 and another of 11 to 100; and the case in which such modes are suitably combined may be cited.

As concerns the (meth)acrylic acid which can be used in the esterification reaction contemplated by this invention, acrylic acid and methacrylic acid may be independently used or they may be used in a mixed state. Their mixing ratio may be selected in an arbitrary range.

From the stoichiometrical point, the mixing ratio of the raw materials mentioned above which may be used in the esterification reaction according to this invention is 1:1 reduced as a molar ratio. Actually, however, it does not need to be particularly restricted so long as it fall in a range in which the esterification reaction of an alcohol with (meth) acrylic acid efficiently proceeds. Generally, for the purpose of expediting the esterification reaction by using either of the raw materials in an excess amount and from the viewpoint of purifying the esterified product as aimed at, the one raw material having a lower boiling point and allowing easier expulsion by distillation than the other raw material may be used in an excess amount. Further, in this invention, since part of the (meth)acrylic acid of a lower boiling point may be distilled and expelled from the reaction system while the water formed by the reaction and the dehydrating solvent are azeotroped during the esterification reaction, the amount of the (meth)acrylic acid to be used (charged) may be preferably in excess of the stoichiometrically calculated amount relative to the amount of the alcohol to be used (charged). Specifically, the amount of the (meth)acrylic acid to be used is generally in the range of 1.0 to 30 mols, preferably in the range of 1.2 to 10 mols, more preferably in the range of 1.5 to 10 mols, and most desirably in the range of 2 to 10 mols, based on 1 mol of the alcohol. If the amount of the (meth)acrylic acid to be used is less than 1.0 mol, based on 1 mol of the alcohol, the esterification reaction would not smoothly proceed and the yield of the esterified product would be insufficient. Conversely, if the amount exceeds 30 mols, the excess would bring no proportionate addition to the yield and only impair the economy of the production.

As concrete examples of the acid catalyst which can be used in the esterification reaction according to this invention, sulfuric acid, methane sulfonic acid, paratoluene sulfonic acid, paratoluene sulfonic acid hydrate, xylene sulfonic acid, xylene sulfonic acid hydrate, naphthalene sulfonic acid, naphthalene sulfonic acid hydrate, trifluoromethane sulfonic acid, "Nafion" resin, "Amberlyst 15" resin, phosphorus tungstic acid hydrate, and hydrochloric acid may be cited. These acid catalysts may be used either singly or in the form of a mixture of two or more members.

In these acid catalysts, the acid catalyst to be used may preferably have a high boiling point under normal pressure in consideration of the azeotropic temperature of the dehydrating solvent and water which will be described specifically herein below and the temperature of the esterification reaction. Typically, the boiling point under normal pressure of the acid catalyst which may be preferably used in this invention is preferably not less than 150° C., more preferably not less than 200° C. Thus, sulfuric acid (boiling point under normal pressure: 317° C.), paratoluene sulfonic acid (boiling point: 185 to 187° C./0.1 mmHg), paratoluene sulfonic acid hydrate, and methane sulfonic acid (boiling point: 167° C./10 mmHg) are preferably used over the rest of acid catalysts. The present inventors have acquired a knowledge that one of the causes for the formation of a diester, i.e., the impurity liable to degrade the quality and performance of the esterified product, is the cleavage of an alkoxy polyalkylene glycol and that the cleavage can be also caused by the acid catalyst. Based on this knowledge, they have found that the acid catalyst which is less liable to the cleavage can be desirably used. In consideration of the point mentioned above, paratoluene sulfonic acid and paratoluene sulfonic acid hydrate may be cited as the acid catalysts which can be particularly advantageously used in this invention.

In the mode described above, the amount of the acid catalyst to be used does not need to be particularly restricted so long as it fall in the range in which the catalytic action sought after can be effectively manifested. It is preferably not more than 0.4 millieqivalent/g, more preferably in the range of 0.36 to 0.01 milliequivalent/g, and particularly preferably in the range of 0.32 to 0.05 milliequivalent/g. If the amount of the acid catalyst to be used exceeds 0.4 milliequivalent/g, the amount of the diester to be formed in the reaction system during the esterification reaction would increase and the cement dispersant synthesized with the esterified product [alkoxy polyalkylene glycol mono(meth) acrylic acid] obtained by the esterification reaction would suffer degraded cement-dispersing properties. In this specification, the amount of the acid catalyst (milliequivalent/g) to be used is expressed by a numerical value obtained by dividing the number of equivalent weight (milliequivalent) of the $H^+$ of the acid catalyst used in the reaction by the total amount (g) of the alcohol and the (meth)acrylic acid as the raw materials. More specifically, it is the numerical value calculated by the following formula.

Amount of acid catalyst used (millequivalent/g) =

$$\frac{[\text{Equivalence (milliequivalent) of } H^+ \text{ of acid catalyst}]}{[(\text{Weight } (g) \text{ of alcohol charged}) + (\text{Weight } (g) \text{ of (meth)acrylic acid charged})]}$$

In this invention, the addition of the acid catalyst to the reaction system may be made collectively, continuously, or successively. Preferably in terms of operational efficiency, the acid catalyst is added collectively together with the raw materials to the reaction tank.

Alternatively, according to this invention, when the esterification reaction is carried out in the presence of an acid catalyst, the acid catalyst may be preferably used in the form of a hydrate and/or an aqueous solution and, at the same time, the amount of the acid catalyst to be used is preferred to satisfy the relation of the following formula:

$$0<Y<1.81X-1.62$$

wherein X (% by weight) represents the weight ratio of the acid in the acid catalyst to the total weight of the alcohol and the (meth)acrylic acid as raw materials and Y (% by weight) represents the weight ratio of the water present in the hydrate and/or the aqueous solution of the acid catalyst to the total weight of the alcohol and the (meth)acrylic acid as raw materials. Specifically, the present inventors have found that one of the causes for the formation of a diester, i.e., the impurity liable to degrade the quality and performance of the esterified product, is the cleavage of an alcohol and that the cleavage can be also caused by the acid catalyst. Based on this knowledge, they have found the above conditions as those for repressing the action of cleaving the alcohol as the raw material while thoroughly retaining the catalytic function of the acid catalyst, and also found that these conditions are capable of repressing the formation of gel during the esterification reaction and enables the resultant esterified product to acquire an exceptionally high quality. It has been further learnt that the esterified product is highly useful as the monomer component, i.e. the raw material for the polymer component to be used in various applications including a pigment dispersant for calcium carbonate, carbon black, ink, and other pigments, and a scale remover, a dispersant for a slurry of gypsum and water, a dispersant for CWM, a thickener, as well as a cement dispersant.

As concrete examples of the acid catalyst which can be used in the mode mentioned above, sulfuric acid, methane sulfonic acid, paratoluene sulfonic acid, xylene sulfonic acid, naphthalene sulfonic acid, trifluoromethane sulfonic acid, "Nafion" resin, "Amberlyst 15" resin, phosphorus tungstic acid, and hydrochloric acid which are invariably used in the form of a hydrate and/or an aqueous solution may be cited. Among other acid catalysts mentioned above, sulfuric acid, paratoluene sulfonic acid, and methane sulfonic acid in the form of a hydrate and/or an aqueous solution may be particularly advantageously used. These acid catalysts may be used either singly or in the form of a mixture of two or more members. Further, the present inventors, as described above, have acquired a knowledge that one of the causes for the formation of a diester, i.e., the impurity liable to degrade the quality and performance of the esterified product, is the cleavage of an alcohol and that the cleavage can be also caused by the acid catalyst and, on the basis of this knowledge, they have found that the acid catalyst which is less liable to the cleavage can be desirably used. Specifically, the acid catalyst that answers this description may be paratoluene sulfonic acid and which is used in the form of a hydrate and/or an aqueous solution.

The amount of the acid catalyst to be used according to the mode described above is only required to be in the range in which the expected catalytic action can be effectively manifested. For the purpose of enabling the action of cleaving the alcohol as the raw material to be repressed as described above, the amount of the acid catalyst to be used is only required to satisfy the following relation:

$$0<Y<1.81X-1.62$$

wherein X (% by weight) represents the weight ratio of the acid in the acid catalyst to the total weight of the alcohol and the (meth)acrylic acid as raw materials and Y (% by weight) represents the weight ratio of the water present in the hydrate and/or the aqueous solution of the acid catalyst to the total weight of the alcohol and the (meth)acrylic acid as raw materials. To describe this requirement by citing a concrete example so as to avoid misunderstanding, in the case of paratoluene sulfonic acid monohydrate, for example, it should be noted that X (% by weight) represents the weight ratio of paratoluene sulfonic acid based on the total weight of the raw materials, and Y (% by weight) represents the weight ratio of the water present as the monohydrate based on the total amount of the raw materials, and that the acid component (such as (meth)acrylic acid as the raw material) and the water components (such as water formed by the esterification reaction) other than the acid catalyst can never constitute themselves X and Y which are referred to herein.

If the amount of the acid catalyst to be used does not satisfy the relation of the formula mentioned above, the following problems would ensue. To be specific, in the case of Y=0, since the acid catalyst does not allow the existence of water in the form of a hydrate and/or an aqueous solution therein, the amount of gel suffered to form in the reaction system during the course of the esterification reaction increases and this increase degrades performance such as cement-dispersing properties used in a cement dispersant synthesized with the esterified product obtained by the esterification reaction. On the other hand, in the case of $Y \geq 1.81X-1.62$, the amount of gel suffered to form in the reaction system during the course of the esterification reaction also increases, which degrades performance such as cement-dispersing properties used in a cement dispersant synthesized with the esterified product obtained by the esterification reaction.

In the mode described above, the acid catalyst may be added to the reaction system collectively, continuously, or successively. In terms of operational efficiency, the acid catalyst may be preferably added collectively together with the raw materials to the reaction tank.

The esterified product by the mode described above may be highly useful as a raw material for a polymer component which is used in various applications such as a pigment dispersant for calcium carbonate, carbon black, ink, and other pigments, and a scale remover, a dispersant for a slurry of gypsum and water, a dispersant for CWM, a thickener, as well as a cement dispersant. Specifically, the formation of gel which causes the occurrence of a high-molecular-weight cross-linked polymer of poor dispersing properties liable to exert adverse effects on the dispersing properties, i.e. the basic property required for such service application can be repressed high effectively.

The esterification reaction according to this invention essentially proceeds in the presence of a polymerization inhibitor. The use of the polymerization inhibitor can prevent the alcohol and the (meth)acrylic acid as the raw materials, the resultant esterified product, and the mixture thereof from being polymerized. The polymerization inhibitor, which can be used in the esterification reaction mentioned above, does not need to be particularly restricted but may be randomly selected from well-known polymerization inhibitors. As concrete examples thereof, phenothiazine, tri-p-nitrophenyl methyl, di-p-fluorophenyl amine, diphenyl picryl hydrazyl, N-(3-N-oxyanilino-1,3-dimethyl butylidene) aniline oxide, benzoquinone, hydroquinone, methoquinone, butyl catechol, nitroso benzene, picric acid, dithiobenzoyldisulfide, cupferron, and-copper (II) chloride may be cited. On account of the solubility in a dehydrating solvent and water formed by the reaction, phenothiazine, hydroquinone, and methoquinone are preferably used over the rest of polymerization inhibitors. These polymerization inhibitors may be used either singly or in the form of a mixture of two or more members.

When the acid catalyst is used in the form of a hydrate and/or an aqueous solution as described above, phenothiazine may be very useful in respect that it not only functions effectively on the gel-forming substance in the aqueous solution existing in the reaction system but also can manifest polymerization inhibiting ability very effectively and can effectively repress the formation of high-molecular-weight products during the expulsion of dehydrating solvent and water by azeotropic distillation after the completion of esterification reaction as will be described specifically herein below without recourse to such a water-soluble polymerization inhibitor as hydroquinone and methoquinone which exhibits a polymerizing activity, though only feebly.

According to the method of this invention, the amount of the polymerization inhibitor to be used is in the range of 0.001 to 1% by weight, preferably in the range of 0.001 to 0.1% by weight, based on the total amount of the alcohol and (meth)acrylic acid as the raw materials. If the amount of the polymerization inhibitor to be used is less than 0.001% by weight, the shortage would be at a disadvantage in manifesting polymerization-inhibiting ability insufficiently and encountering difficulty in effectively preventing the alcohol and the (meth)acrylic acid as the raw materials, the consequently formed esterified product, or the mixture thereof from being polymerized. On the other hand, if the amount of the polymerization inhibitor to be used exceeds 1% by weight, the excess would be at a disadvantage in impairing the quality and performance of the consequently formed esterified product owing to an increase in the amount of the polymerization inhibitor suffered to persist therein and imposing a burden on the economy of production without bringing any proportionate addition to the effect.

The esterification reaction according to this invention, for the reason offered herein below, must be carried out with a dehydrating solvent added. When the esterification reaction is carried out without using a dehydrating solvent, namely in the absence of a solvent, the reaction solution is subjected to bubbling treatment with air and the like for the purpose of removing therefrom water formed by the reaction. Since the raw materials are directly heated from a heat source in the absence of a solvent, this heating probably induces cleavage of alcohol and gives rise to a diester and results in degradation of cement dispersing ability. The term "dehydrating solvent" as used herein is defined as a solvent capable of forming an azeotrope with water. By the use of the dehydrating solvent, water formed by the esterification reaction can be very efficiently removed by distillation from the reaction solution because it readily forms an azeotrope with this solvent. As concrete examples of the dehydrating solvent, benzene, toluene, xylene, cyclohexane, dioxane, pentane, hexane, heptane, chlorobenzene, and isopropyl ether may be cited. These dehydrating solvents may be used either singly or in the form of a mixture of two or more members. Among other dehydrating solvents mentioned above, those which have azeotropic temperatures with water of not more than 150° C., more preferably in the range of 60° to 90° C., may be used preferably. As concrete examples of the dehydrating solvent which answer this description, cyclohexane, toluene, dioxane, benzene, isopropyl ether, hexane, and heptane may be cited. If the azeotropic temperature of a given dehydrating solvent with water exceeds 150° C., this solvent would prove unfavorable in terms of handling (including such controls as the management of temperature in the reaction system during the course of reaction and the treatment of the azeotropic mixture for condensation and liquefaction).

Preferably, the dehydrating solvent effects expulsion of the water formed by the reaction from the reaction system by forming an azeotropic mixture thereof and then refluxes itself through the reaction system while condensing and liquefying water formed by the reaction and thereby separating and removing the consequently formed water condensate from the reaction system. In this case, the amount of the dehydrating solvent to be used is in the range of 1 to 100% by weight, preferably in the range of 2 to 50% by weight, based on the total amount of the alcohol and the (meth)acrylic acid as the raw materials to be charged. If the amount of the dehydrating solvent is less than 1% by weight, the shortage would be at a disadvantage in producing no fully satisfactory removal from the reaction system of water formed by the reaction during the course of the esterification reaction and preventing the esterification reaction from proceeding smoothly. If the amount of the dehydrating solvent to be used exceeds 100% by weight, the excess would be at a disadvantage in producing no proportionate addition to the effect and requiring a great deal of heat for keeping the reaction temperature constant and consequently impairing the economy of the production.

Though the esterification reaction can proceed in batchwise or continuously, this invention prefers this reaction to be performed in batchwise.

In this invention, it is essential that the esterification reaction be carried out at a reaction temperature of not higher than 130° C., preferably in the range of 30° to 125° C., more preferably in the range of 100° to 125° C., most preferably in the range of 110° to 120° C. If the reaction temperature exceeds 130° C., the excess would be at a disadvantage in forming an unduly large amount of impurities (mainly diester) owing to the cleavage of polyalkylene glycol, consequently compelling the cement dispersant made from the esterified product containing the impurities to suffer from degradation of cement-dispersing properties, and impairing the performance and property of the resultant esterified product as by inducing polymerization of the raw materials and increasing the amount of the raw materials to mingle into the azeotropic mixture. Conversely, if the temperature is lower than 30° C., the shortage would be at a disadvantage in retarding the reflux of the dehydrating solvent, though without entailing the formation of impurities, and consequently causing the dehydration to consume immense time and allowing the esterification reaction to advance smoothly only with difficulty besides extremely lowering the speed of formation of the water by the reaction.

In this invention, it is essential that the esterification reaction be carried out at a solvent circulating speed of not less than 0.5 cycle/hour, preferably in the range of 1 to 100 cycles/hour, more preferably in the range of 1 to 50 cycles/hour, most preferably in the range of 1 to 20 cycles/hour. If the solvent circulating speed is less than 0.5 cycle/hour, the shortage would be at a disadvantage in suffering the dehydration speed with the dehydrating solvent (the speed of expelling by distillation water generated by the reaction from the reaction system) to be lower than the speed of water generated by the reaction and allowing the water resulting from the reaction and stagnating in the reaction system (reaction tank) to grow gradually with time and consequently inducing a decline in the velocity of reaction and markedly elongating the reaction time as in the conventional method. If the solvent circulating speed exceeds 100 cycles/hour, the excess would be at a disadvantage in impairing economy of the production by requiring supply of a large amount of energy (heat) to the reaction system and necessitating a large dimensional addition to the heating device notwithstanding that the water formed by the reaction during the course of the reaction may be sufficiently removed from the reaction system owing to the sequential expulsion of this water from the reaction system by the distillation of the azeotropic mixture.

By performing the esterification reaction at a prescribed reaction temperature at a prescribed solvent circulating speed as described above, the formation of impurities in the reaction system can be repressed without requiring the reaction temperature to be elevated to a zone in which impurities are easily formed (a zone exceeding 130° C.). Further, this invention, by increasing the solvent circulation speed, enables the water formed by the reaction to be efficiently expelled in the form of an azeotropic mixture from the reaction system without entailing protracted retention of the water within the reaction system and, owing to the fact that the equibratory reaction proceeds in the direction of the esterification, allows the reaction time to be shortened.

The expression "a solvent circulating speed during the esterification reaction" as used in the present specification means as below. To be specific, "one cycle" is defined as a time required for circulating a distillate in an amount equal to a total amount (by volume) of a dehydrating solvent initially placed in the reaction system, when a dehydrating solvent is placed in the total amount (by volume), expelled by distillation from the reaction system while the esterification reaction is in process and the distillate is condensed and liquefied and circulated back to the reaction system, more specifically, when a dehydrating solvent is expelled from the reaction system azeotropically with water formed by the reaction (occasionally referred to simply as the "reaction-forming water" in the present specification) during the course of the esterification reaction, the reaction-forming water is separated and removed from the condensed and liquefied distillate, and the rest of the distillate (mainly the dehydrating solvent) is circulated back to the reaction system. The solvent circulating speed during the esterification reaction is expressed by the number of such cycles per unit time (one hour) with the denomination of "cycle/hour". When the amount of the distillate circulated in five hours reaches 15 times the total amount of the dehydrating solvent initially placed in the reaction system, for example, the solvent circulating speed is calculated as 3 cycles/hour. By the same token, when the amount of the distillate thus circulated in two hours reaches one half of (0.5 times) the total amount of the dehydrating solvent initially placed in the reaction system, the solvent circulating speed is calculated as 0.25 cycle/hour. Incidentally, the substances that are circulated at all while the dehydrating solvent in the reaction system is expelled from the reaction system by distillation, condensed and liquefied, and circulated back to the reaction system (substances to be circulated) may include, though in a minute amount, various additives such as raw materials with a low boiling point (mainly (meth)acrylic acid as a raw material) liable to be expelled from the reaction system by distillation and a antigelling agent (a polymerization inhibitor or a solvent containing the polymerization inhibitor) to be incorporated in the reaction system for the purpose of preventing the distilled raw material from forming gel and turning into harmful impurities. When such additives as an antigelling agent are used, therefore, it is commendable to adjust conditions of the esterification reaction properly in consideration of the possibility of these additives varying the solvent circulating speed with the advance of the esterification reaction.

The reaction temperature and the solvent circulating speed mentioned above can be adjusted in respectively required ranges by the method (means) of heating the reaction system, the temperature (quantity of heat) applied to the reaction system by the use of the means, the amount of the dehydrating solvent to be placed relative to the raw materials in the reaction system, and etc. As demonstrated in the working examples to be cited herein below, (1) the reaction temperature alone can be varied while the solvent circulating speed is kept constant (fixed) or, conversely (2) the solvent circulating speed alone may be varied while the reaction temperature is kept constant (fixed). The reaction temperature and the solvent circulating speed mentioned above may be arbitrarily set and altered by suitably combining the items (1) and (2) mentioned above. For adjusting the reaction temperature and the solvent circulating speed mentioned above in respectively required ranges as mentioned in the item (1) above, it suffices to place the dehydrating solvent in a relatively small amount in the reaction tank, varying the internal temperature of the reaction tank by changing the temperatures of an external jacket and an internal heater as heat sources of the reaction system, and adjusting the difference between the temperature of the heat source and the internal temperature of the reaction tank thereby fixing the solvent circulating speed. Then, for adjusting the reaction temperature and the solvent circulating speed mentioned above in respectively required ranges as mentioned in the item (2) above, it suffices to place the dehydrating solvent in a relatively large amount in the reaction tank and retain the internal temperature of the reaction tank substantially at a fixed level despite of change of the temperatures of an external jacket and an internal heater as heat sources for the reaction system. The term "reaction temperature" as used herein means the highest (maximum) temperature in the reaction system. Specifically, depending on designs of devices (such as, for example, an external jacket and an internal heater) to be used as heating means, the temperature (reaction temperature) in the reaction system (reaction tank) is scattered depending on positions in the reaction system, elevated with the advance of the esterification reaction, and varied with time. Since the elevation of the reaction temperature entails the formation of impurities, it is important that the reaction temperature be prevented from surpassing the upper limit defined above, without reference to the conditions of position and time and irrespectively of the choice of position and time. The present invention has elected to define this upper limit by the highest temperature mentioned above.

Further, the method (means) for expelling a dehydrating solvent from a reaction system by distillation, condensing and liquefying the distillate, and circulating the condensate back to the reaction system during the course of the esterification reaction and the apparatus (mechanism) for implementing the method do not need to be restricted particularly. They may be properly selected among well-known methods (means) and apparatus and put to use as suitably combined. For example, an apparatus which, as illustrated in FIG. 1 to be specifically described herein below, is composed mainly of a combination of a heat exchanger, a cooling device, and a condenser as means and device for condensing and liquefying the gaseous distillate, a liquid-liquid separator as means and device for dividing the liquefied distillate into two layers, i.e., a water phase and a solvent phase, and separating the layers from each other, a pump as means and device for removing the water phase (reaction-forming water) out of the reaction system, a pump as means and device for returning the dehydrating solvent of the solvent phase back to the reaction system under pressure, and pipes as transportation means and device for interconnecting the component devices may be cited as a concrete example. Further, the means and devices including a reaction system are generally provided with a proper control mechanism (comprising various sensors for sensing temperature, pressure, flow volume-flow rate, and liquid level, a main control part for processing information (electric signals) received from the sensors, and issuing commands (electric signals) to operating parts thereby controlling the operating parts, and an operating part effecting required control in accordance with issues from the control part (using temperature adjusting means (e.g., heater), valves for adjusting pressure and flow volume, and level controllers for keeping the liquid level in the reaction tank constant)). The devices which can be used for the various means mentioned above do not need to be particularly limited. Naturally, the devices cited specifically above may be substituted with such devices as are suitably selected among various devices well-known to the art. It is naturally permissible to combine other means and devices known to the art or adopt suitably methods which resort to the alternatives of such other means and devices in place of the devices cited above without departure from the objects and scopes of this invention which consist in expelling the dehydrating solvent from the reaction system by distillation, condensing and liquefying the distillate, and circulating the resultant condensate back to the reaction system. It is also allowable to add supplementarily to the construction described above an additive feeding mechanism provided with a dropping or spraying nozzle as means and device for putting the antigelling agent to work and a vacuum pump as means and device for expelling the dehydrating solvent from the reaction system by distillation, condensing and liquefying the distillate, and expelling the condensate out of the reaction system. As means and device (mechanism) for measuring the aforementioned solvent circulating speed, it is commendable to construct a flow volume measuring system capable of measuring an accumulated flow volume and suitable for the measurement of the solvent circulating speed defined above and install the flow volume measuring part (such as, for example, a flow meter) on the path for returning to the reaction system the solvent phase which remains after the separation and removal of the water phase. Although the flow volume measuring part can be installed on the path which is positioned before the separation and removal part of the water phase, in such a case, the distillate flowing inside this path contains reaction-forming water. This mode, however, is not called a wise measure because it is not readily feasible as evinced by the fact that the measurement of an amount of component circulated exclusively requires to estimate the composition of the distillate based on a azeotropic temperature and a fluid state of the distillate (gas-liquid state and temperature) and the calculation of a solvent circulating speed requires to prepare, based on numerous calculation data, complicated calculation programs which are variable with kinds of raw materials.

Of the conditions for the esterification reaction according to this invention, those concerning the reaction temperature have been as already described above. Other conditions are only required to allow the esterification reaction to proceed smoothly. The reaction time, as described specifically herein below, has to be such that the ratio of esterification reaches at least 70%, preferably at least 80%. The time which answers this description is in the range of 1 to 50 hours, preferably 3 to 40 hours. Though the esterification reaction according to this invention is permitted to proceed under normal pressure or under a reduced pressure, it may preferably proceed under normal pressure from the viewpoint of equipment.

Properly, the ratio of esterification in the esterification reaction according to this invention is not less than 70%, preferably in the range of 70 to 99%, and more preferably in the range of 80 to 98%. If the ratio of esterification is less than 70%, the shortage would be at a disadvantage in forming the esterified product (alkoxy polyalkylene glycol mono(meth)acrylic acid) with an insufficient yield and compelling the cement dispersant made from this product as a raw material to suffer from poor cement-dispersing properties. The term "ratio of esterification" as used in this specification is a numerical value which is found by measuring the amount of alcohol, one of the starting materials for esterification, to be decreased under the following conditions for the measurement of esterification and calculating the following formula using the result of the measurement.

Esterification ratio (%)={[(Area of alcohol charged)−(Area of alcohol at completion of esterification)]/[Area of alcohol charged]}×100

<Condition for measurement of esterification>

Analyzing device: Chromatography Manager made by Waters and sold under the trademark designation of "Millennium"

Detector: Detector made by Waters and sold under the product code of "410 RI"

Column used: Three columns made by GL Science and sold under the trademark designation of "Inatosil ODS-2"

Column temperature: 40° C.

Eluate: Prepared by mixing 8946 g of water, 6000 g of acetonitrile, and 54 g of acetic acid and adjusting the mixture with an aqueous 30% sodium hydroxide solution to pH 4.0

Flow rate: 0.6 ml/min

Since the ratio of esterification is determined by the formula described above, the ratio of esterification can never exceed 100%. In this invention, therefore, the time at which the ratio of esterification reaches a level above the prescribed level is reported as marking completion of the esterification reaction.

In the production method according to this invention, it is commendable to expel the reaction-forming water from the reaction system by distillation and, at this time, to cause an antigelling agent to act on the distillate containing the reaction-forming water for the purpose of enabling a raw material with a low boiling point distilled together with the reaction-forming water as described above to repress the polymerization which occurs during the course of condensation and also repress the formation of gel as in a flange part of a pipe ascending from the reaction tank forward the condenser, namely the clogging in a tube of a condenser and a connecting pipe between a reaction tank and a condenser. The antigelling agent may be used similarly to the polymerization inhibitor which is used for the same purpose in the reaction system. As described therein, it does not need to be particularly restricted but may be suitably selected among various antigelling agents well-known to the art. As concrete examples of thereof, phenothiazine, tri-p-nitrophenyl methyl, di-p-fluorophenyl amine, diphenyl picryl hydrazyl, N-(3-N-oxyanilino-1,3-dimethyl butylidene) aniline oxide, benzoquinone, hydroquinone, methoquinone, butyl catechol, nitroso benzene, picric acid, dithiobenzoyl disulfide, cupferron, and copper (II) chloride may be cited. Among other antigelling agents mentioned above, phenothiazine, hydroquinone, and methoquinone may be used favorably on account of the solubility in a dehydrating solvent and water formed by the reaction. These antigelling agents may be used either singly or in the form of a mixture of two or more members.

The amount of the antigelling agent to be added has only to match the amount of the raw material of a low boiling point to be distilled, depending on conditions of the esterification reaction, particularly the quantity of heat applied to the reaction system and the amount of the dehydrating solvent to be initially placed in the reaction system, namely may be such an amount as to enable a raw material of a low boiling point which is successively distilled from the time of starting distillation of the azeotropic mixture to the time of completing the esterification reaction to prevent the formation of gel constantly. By adding the antigelling agent in an amount in the range of 0.1 to 1000 ppm, preferably 1 to 500 ppm, based on the combined amounts of alcohol and (meth) acrylic acid to be initially placed in the reaction tank as the raw materials, the object mentioned above can be accomplished. If the amount of the antigelling agent to be added is less than 0.1 ppm based on the combined amounts of the raw materials initially placed, the shortage would possibly entail formation of a gel-like substance. This amount may well be called insufficient for the purpose of effectively manifesting polymerization inhibiting properties constantly on raw materials of low boiling points which are successively distilled from the time of starting distillation of azeotropic mixture to the time of completing the esterification reaction. If the amount of the antigelling agent conversely exceeds 1000 ppm based on the combined amounts of the raw materials initially placed, the excess would be at a disadvantage in being unduly large for effective manifestation of the gel formation preventing properties (polymerization inhibiting properties) and impairing the economy of production without bringing a proportionate addition to the effect. When the total amount of the antigelling agent intended to be used is placed all at once in the reaction system, the raw material of a low boiling point which is successively distilled from the time of starting distillation of the azeotropic mixture to the time of completing the esterification reaction cannot be effectively prevented from forming gel. It is commendable, therefore, to add the antigelling agent piecemeal in a fixed amount successively (continuously) from the time of starting distillation of the azeotropic mixture to the time of completing the esterification reaction in response to the distillation of the azeotropic mixture until the amount finally reaches a total in the range mentioned above.

The manner for causing an antigelling agent to act as expected (including a mode of action and an acting region) does not need to be particularly restricted so long as this agent be enabled to act (by contact) effectively on raw materials of low boiling points (fluid substances) distilled from the reaction system. When the reaction-forming water is to be expelled by distillation from the reaction system, the antigelling agent is preferred to be capable of being distilled at the lowest permissible temperature from the viewpoint of handling. For this purpose, a method of initially charging the reaction system with a solvent capable of forming an azeotropic mixture with the reaction-forming water (in the present specification, occasionally referred to simply as "dehydrating solvent") and causing the dehydrating solvent to be distilled in the form of an azeotropic mixture with the reaction-forming water (in the present specification, occasionally referred to briefly as "solvent-water azeotropic mixture") during the course of the reaction is generally practiced. In this respect, it is commendable to add a solution of an antigelling agent in a solvent similar in kind to the dehydrating solvent so that it may promptly act on the solvent-water azeotropic mixture containing a raw material of a low boiling point (namely it may, during the condensation (liquefaction) of the solvent-water azeotropic mixture containing low boiling raw materials, promptly contact with the liquefied product and attain intimate solution or dispersion in the dehydrating solvent containing raw materials of a low boiling points which are susceptible of gelation.

Now, preferred methods for acting an antigelling agent mentioned above will be described below with reference to respective modes of action. This invention allows proper combination of these methods and suitable adoption of the other acting methods owell-known to the art. The acting methods illustrated herein below may be typical examples cited for the purpose of enabling persons of ordinary skill in the art to understand this invention easily. Naturally, this invention should not be limited to or by these examples.

1. Method for Adding the Agent in a Liquefied (dissolved) State:

A solution of an antigelling agent in a proper solvent, preferably a solvent similar in kind to the dehydrating solvent initially placed in the reaction system, may be added dropwise or sprayed to a region for condensing a distillate containing reaction-forming water (preferably, a solvent-water azeotropic mixture), specifically to an interior of a condenser for condensing and liquefying a distillate containing reaction-forming water, preferably from an upper part of a condenser (especially a column top) to the interior thereof in such a manner as to establish parallel contact with the distillate. It may be otherwise permissible, though depending on such factors as a type of condenser used, to place initially a solution containing an antigelling agent in a condenser and then blow a distillate in a gaseous state or cast a distillate in a liquefied state into the condenser so as to effect contact (intimate solution or dispersion) with the solution held therein.

2. Method for Adding the Agent in a Solidified State:

An antigelling agent in a powdery state may be dropped or sprayed onto a region for condensing a distillate containing reaction-forming water, specifically to an interior of a condenser for condensing and liquefying a distillate containing reaction-forming water, preferably from an upper part of a condenser (especially a column top) to the interior thereof in such a manner as to establish parallel contact with the distillate. It may be otherwise permissible, though depending on such factors as a type of condenser, to have an antigelling agent in the form of particles of a fixed particle diameter placed in advance in the condenser and then exposed to the distillate for required contact.

3. Method for Adding the Agent in a Gasified State:

An antigelling agent in a gasified state (incluing a sublimated state) may be supplied into a pipe connecting between the reaction system and the condenser and mixed therein, prior to the condensation and liquefaction of a gaseous distillate containing reaction-forming water (including a raw material of a low boiling point).

Concerning the liquefaction of Item 1. mentioned above, when an antigelling agent is caused to manifest its action in a dissolved state, the solvents which can dissolve the antigelling agent mentioned above include benzene, toluene, xylene, cyclohexane, acetone, methylethyl ketone, n-hexane, and heptane, for example. It is commendable, however, to use a solvent similar in kind to the dehydrating solvent which is initially placed in the reaction system as mentioned above. When different solvents are used, they need to be separately recovered during the reflux back to the reaction system. Alternatively, when the heat transfer coefficient of the mixed solvents equals the heat transfer coefficient of the solvent initially placed in the reaction system, it becomes necessary to adjust the quantity of heat given to the reaction system lest the amount of the reaction-forming water to be distilled (speed of distillation) should vary widely, during the reflux back to the reaction system. In the case of different solvents used, their use possibly complicate the control and management of the reaction system. Thus, it is safe to conclude that the use of two solvents similar in kind is commendable.

Also when an antigelling agent is caused to function by being dissolved in a solvent (preferably a dehydrating solvent), for the purpose of repressing the occurrence of a gel-like substance, it suffices to supply an antigelling agent in such a manner to a raw material of a low boiling point (in a gaseous or liquid state) passing an interior of a condenser that it may exist constantly and function effectively in the raw material. The mixing ratio of the antigelling agent and the solvent does not need to be particularly restricted. Generally, the amount of the antigelling agent is in the range of 0.001 to 10 parts by weight, preferably 0.01 to 5 parts by weight, based on 100 parts by weight of the solvent. If the mixing ratio is such that the amount of the antigelling agent is less than 0.001 part by weight based on 100 parts by weight of the solvent, since the amount of the antigelling agent to be added is fixed relative to the total amount of the raw materials initially placed in the reaction system as defined above, the amount of the solvent to be used (the total amount to be added) would increase and the amount of the solvent relative to the amount of the dehydrating solvent initially placed would grow due to successive reflux. The control and management of the reaction system, therefore, is inevitably complicated because it becomes necessary to adjust the quantity of heat given to the reaction system and prevent the amount of the reaction-forming water to be distilled (speed of distillation) from varying widely. When a solvent to be used is not similar to the dehydrating solvent and these solvents are separately recovered, the cost of recovery would be increased and the cost of production is enlarged. Conversely, if the mixing ratio is such that the amount of the antigelling agent exceeds 10 parts by weight based on 100 parts by weight of the solvent, since the amount of the solvent to be used (the total amount to be added) is conversely decreased, the amount of the solvent added per unit time would be restricted, the frequency of contact of the antigelling agent with the raw material of a low boiling point would be relatively lowered, the raw material of a low boiling point would be liquefied without making the contact with the antigelling agent, and thus the effective repression of the formation of a gel-like substance will become difficult. For the purpose of securing the amount of the solvent required to be added per unit time, the cost of production is increased because the antigelling agent is required in an amount larger than the amount defined above relative to the initially placed raw materials.

The method for producing the esterified product according to this invention will be described below with reference to FIG. 1.

FIG. 1 is a schematic diagram of the construction of a typical apparatus to be used for the method for producing the esterified product according to this invention.

As shown in FIG. 1, the construction of the apparatus according to the present embodiment is provided with a reaction tank 101 which is provided as a heating means for effecting the esterification reaction (such as, for example, a direct heating method resorting to an internal heater or an indirect heating method resorting to an external jacket) with an external jacket 102 using pressurized steam, for example, as a heating medium. In this case, the material for the internal part of the reaction tank is not particularly restricted but may be selected among conventional materials. The materials of SUS may be cited as examples, those of the species of SUS 304, SUS 316, and SUS 316L as examples preferable in terms of corrosion-proofness, and those of the species of SUS 316 and SUS 316L as more preferable examples. The reaction tank may be lined with glass so as to be inactivated relative to the raw materials and the product by esterification. To the reaction tank 101, a raw material storage tank 103 made of stainless steel (such as, for example, SUS 316) for alkoxy polyalkylene glycol as a raw material and a raw material storage tank 105 for (meth)acrylic acid, a catalyst storage tank 107 for an acid catalyst for reaction, a polymerization inhibitor storage tank 109 for storing a polymerization inhibitor for preventing the polymerization in the reaction system (reaction tank 101), and a neutralizer storage tank 111 made of carbon steel (such as, for example, high carbon steel) and used for storing a neutralizing agent (an aqueous solution of a neutralizing agent) intended for neutralizing the catalyst after the esterification reaction are connected respectively with pipes 113, 115, 117, 119, and 121. Since (meth)acrylic acid is easily polymerized and polymerized even in consequence of protracted storage or exposure to heatand, for example, a minute amount of a polymerization inhibitor (such as 0.1% hydroquinone) may be added. In addition, since it also becomes readily polymerizable through the phenomenon of crystallization, when it is preserved in the raw material storage tank 105, benzene may be added to prevent (meth)acrylic acid from crystallization. Alternatively, (meth)acrylic acid as a raw material may be circulated through a circulating path 151 while constantly retained at 30° to 40° C. so as not to be polymerized, by forming the path 151 provided with an external jacket 150 (insulating means) using a pump 116 as illustrated in FIG. 1 to keep the (meth)acrylic acid constantly at a temperature in the range of 30° to 40° C. The raw material storage tank 105 for (meth)acrylic acid, the pipe 115, the pump 116, and the circulating path 151 may be lined with such a corrosion-proofing material as a synthetic resin for the purpose of protection against the corrosion by (meth)acrylic acid which has a corroding property. Likewise, the catalyst storage tank 107 and the pipe 117 therefor may be lined with such an acid-resistant material as a synthetic resin for the purpose of protection against the corrosion by the acid catalyst. To the lower part of the reaction tank 101 mentioned above, a pipe 153 is connected for recovering the esterified product synthesized inside the reaction tank 101 by the esterification reaction (or, in the case of a cement dispersant, for example, the polymer obtained by further polymerizing the esterified product as a monomer component in the reaction tank 101). Inside the reaction tank 101, a plurality of temperature sensors (not shown) for measuring the reaction temperature may be mounted at as many proper sites. These temperature sensors may be electrically connected to a control part for controlling a mechanism required to maintain the reaction temperature at a prescribed level (not higher than 130° C., preferably in the range of 30° to 125° C.) (for example, a temperature of the jacket 102 mounted on the reaction tank 101).

Further, in this embodiment, as a mechanism (an apparatus) for expelling by distillation a distillate containing reaction-forming water to be formed during the esterification reaction in a reaction system (a reaction tank 101), condensing and liquefying the distillate while preventing the occurrence of gel, separating and removing the reaction-forming water, and returning the rest of the distillate at the solvent circulating speed defined above (not less than 0.5 cycle/hour, preferably in the range of 1 to 100 cycles/hour), a circulation system is provided therein for condensing and liquefying by the action of a antigelling agent a distillate occurring as an azeotropic mixture of reaction-forming water and a dehydrating solvent, separating and removing the reaction-forming water (water phase) from the condensed and liquefied distillate, and refluxing the rest of the condensate (a solvent phase mainly containing the dehydrating solvent) back to the reaction tank 101 at the solvent circulating speed mentioned above. To be more specific, the upper part of the reaction tank 101 and the top part of the column of a vertical shell and tube type condenser 125 of the counterflow (or parallel flow) contact type are connected with a pipe 123. The lower bottom part of the condenser 125 and the upper part of a water separator 127 made of SUS are connected with a pipe 129. Inside the water separator 127, a partition plate 131 is formed. The partition plate 131 divides the interior of the water separator 127 into two chambers 133 and 134. The lower part of the chamber 133 intended for storing the distillate condensed and liquefied in the condenser 125 and a treating tank 135 for the reaction-forming water are connected with a pipe 137. To the treating tank 135, a pipe 139 for waste water is connected. The lower part of the other chamber 134 of the water separator 127 and the reaction tank 101 are connected with a pipe 141. To this pipe 141, a pipe 145 which is connected to a dehydrating solvent storage tank 143 for storing a dehydrating solvent destined to form an azeotropic mixture with reaction-forming water in the reaction tank 101 is joined (connected). On a pipe 141 before this joining part (on the water separator 127 side), a circulating pump 142 is installed. A flow meter 144 is provided on the pipe 141 after the joining point (on the reaction tank 101 side). To the flow meter 144, a main body of a flow volume measuring system (not shown) is electrically connected for adding a flow volume and computing a solving circulating speed. A spray nozzle 126 is disposed on the top part of the column of the condenser 125 and this spray nozzle 126 is connected through the medium of a pipe 149 to a antigelling agent storage tank 147 for storing an antigelling agent intended to prevent a distillate from forming gel. Then, to the water separator 127, a vacuum pump (ejector) 155 intended to expel by distillation and remove the dehydrating solvent is attached through the medium of a pipe 157 for the purpose of isolating the esterified product after the esterification reaction.

This invention permits use of any of various known materials such as, for example, the materials of Class SUS including the species of SUS 304, SUS 316, and SUS 316L and carbon steel (CS) as well for the condenser. Preferably, for the purpose of repressing the occurrence of gel, a condenser to be used may have the inner wall thereof polished in mirror finish or lined with glass. In consideration of the cost to be required for fabrication and maintenance, the condenser may be preferably made of SUS 304 (equivalent to SUS 27 specified by Japanese Industrial Standard <JIS>; omitted herein below), SUS 316 (equivalent to SUS 32 specified by JIS; omitted herein below), or SUS 316L (equivalent to SUS 33 specified by JIS; omitted herein after), preferably SUS 316 or SUS 316L. Even by the use of the condenser of this kind, the formation of gel can be effectively prevented. The heat transfer surface area of the condenser which may be advantageously used in this invention, though variable with such factors as a volume of a reaction tank, is in the range of 50 to 500 m$^2$, preferably in the range of 100 to 200 m$^2$, in the case of a reaction tank having an inner volume of 30 m$^3$, for example. The cooling medium to be used in the condenser of this invention includes water or oil, for example.

The method for the production of the esterified product according to this invention is carried out as follows by using the apparatus constructed as described above.

First, alcohol and (meth)acrylic acid as raw materials, an acid catalyst, a polymerization inhibitor, and a dehydrating solvent are supplied (charged) from the raw material storage tanks 103 and 105, the catalyst storage tank 107, the polymerization inhibitor storage tank 109, and the dehydrating solvent storage tank 143 through the pipe 141 via the pipes 113, 115, 117, 119, and 145 into the reaction tank 101 respectively in the prescribed amounts and are subjected to esterification reaction under the conditions of esterification (reaction temperature, jacket temperature, and pressure) as specified above. The water successively formed by the esterification reaction forms an azeotropic mixture with the dehydrating solvent placed in the reaction tank 101 and expelled through the pipe 123 by distillation. The solvent-water azeotropic mixture in the form of a gas stream so distilled out is delivered to the condenser 125 and condensed and liquefied therein. For the purpose of preventing the raw material of a low boiling point contained in the azeotropic mixture from gelation during the condensation and liquefaction, the antigelling agent is continuously dropped in the amount specified above from the antigelling agent storage tank 147 via the pipe 149 into the condenser 125 through the spray nozzle 126 provided in the top part of the column thereof and brought into parallel contact with the azeotropic mixture (including both the gas stream and the condensed and liquefied product). The condensed and liquefied azeotropic mixture (including the antigelling agent introduced dropwise) is forwarded from the lower part of the condenser 125, passed through the pipe 129, and stored in the chamber 133 of the water separator 127 and separated therein into the two layers of water phase and solvent phase. The reaction-forming water in the lower layer part is successively extracted from the lower part of the chamber 133 through the pipe 137 and stored in the treating tank 135 for the reaction-forming water. Then, inside the treating tank 135, the reaction-forming water, when necessary, is treated chemically or biologically so as to satisfy the environmental criteria (waste water quality standard) and then released from the system via the pipe 139. Meanwhile, the solvent phase (including the antigelling agent introduced dropwise and the raw material of a low boiling point) of the upper layer part overflows the partition plate 131 and collects in the adjoining chamber 134. Then, the solvent phase is forwarded by the pump 142 from the lower part of the chamber 134 and refluxed back via the pipe 141 to the reaction tank 101 at the solvent circulating speed specified above.

In this invention, the site for installing the antigelling agent storage tank intended to supply the antigelling agent is not particularly restricted but is preferred to be a position at which the formation of gel is liable to occur. For example, in addition to the embodiment illustrated in FIG. 1, namely the embodiment in which the spray nozzle 126 for spraying the antigelling agent is provided in the top part of the column of the condenser 125, the embodiment in which the spray nozzle for spraying the antigelling agent is installed at one or more points on the pipe 123 intervening between the reaction tank 101 and the condenser 125 may be cited. In the latter embodiment, the site to be selected for installing the spray nozzle for spraying the antigelling agent on the pipe 123 may be the position prone to the occurrence of gel such as, for example, the condensing part inside the condenser, the joint part (flange part) between the reaction tank and the line for guiding the rising vapor, the flange part interposed between the vapor line and the top part of the column of the condenser, the thermometer provided on the reaction tank, or the projecting part formed around the inspection window. Among other positions mentioned above, the condensing part inside the condenser, the flange part between the reaction tank and the vapor rising line, and the flange part between the vapor line and the top part of the column of the condenser prove particularly advantageous.

After the completion of the esterification reaction (the time when the ratio of esterification reaches a level above the normality is reported as an end point), an aqueous solution of a neutralizing agent from the neutralizing agent storage tank 111 is added into the reaction tank 101 via the pipe 121 to neutralize the acid catalyst, expel the dehydrating solvent (plus excess (meth)acrylic acid) in the form of an azeotropic mixture with water under normal pressure, and isolate the esterified product as expected. The expulsion of the dehydrating solvent and the excess (meth)acrylic acid by distillation can be attained by using a part of the above mechanism (construction) for releasing the distillate containing water formed during the course of the esterification reaction inside the reaction system (the reaction tank 101), condensing and liquefying the released distillate while precluding the formation of a gel-like substance, then separating and removing the reaction-forming water, and refluxing the rest of the distillate. Incidentally, in this case, since the dehydrated solvent (containing the excess (meth)acrylic acid when the isolation is continuously carried out without entailing polymerization) must be removed from the system without being refluxed, this removal may be accomplished by using the vacuum pump (ejector) 155 which is mounted on the water separator 127. The resultant effluent may be either discarded or reused after the chemical treatment performed in a device separated from the system. Meanwhile, the esterified product obtained by isolation is recovered via the pipe 153. When this product is to be used for the synthesis of a cement dispersant, for example, the esterified product so obtained may be further polymerized as one of the monomer components in the reaction tank 101 to synthesize a polymer capable of serving as a main component of the cement dispersant. In this case, the unaltered (meth)acrylic acid remaining in consequence of excess addition may be preferably used in its unmodified form as another monomer component without being separated and removed.

The embodiment of the method of this invention for the production of the esterified product has been described with reference to FIG. 1. The method for the production of the esterified product according to this invention is not limited to this embodiment described above. It is not restricted at all in terms of procedure (means) and construction of apparatus so long as it be capable of setting the reaction temperature at not higher than 130° C. and the solvent circulating speed at not less than 0.5 cycle/hour. The process and the construction of apparatus to be adopted for the use in the present invention can be suitably selected among those known to the art.

The esterification reaction according to this invention has been described in detail above. After the esterification reaction mentioned above has been finished, the esterified product aimed at may be preferably obtained by neutralizing the whole of the acid catalyst which will be described specifically herein below either alone or in combination with part of the (meth)acrylic acid (partial neutralization step) and then expelling by distillation the dehydrating solvent in the form of an azeotropic mixture with water from the reaction solution which will be described specifically herein below (solvent-expelling step).

Now, the partial neutralization step according to this invention will be described below. When the esterification reaction is carried out in the presence of an acid catalyst in the esterification step mentioned above, it is commendable to perform a partial neutralization step to be described below. The present inventors have found that when water is added to produce an azeotrope at the step of expelling the dehydrating solvent after the esterification reaction or when adjusting water is added to produce the aqueous solution of the esterified product after the esterification reaction in order to perform the additional polymerization using the esterified product, the acid catalyst would cause hydrolysis and induce degradation of quality and performance of the esterified product, that the product by this hydrolysis (hereinafter occasionally referred to simply as "hydrolyzate") remains in the esterified product, and when used for synthesizing a polymer for the production of varying kinds of dispersants including a cement dispersant and thickeners, constitutes itself an extraneous substance which refuses participation in the polymerization, results in lowering the ratio of polymerization (and consequently the productivity), and leads to degradation of the quality and performance of the polymer, and that for solving this problem, it is commendable to neutralize the acid catalyst with an alkali at a temperature of not higher than 90° C. after the completion of the esterification reaction as mentioned above. This neutralization step permits the formation of the esterified product of high purity and high quality without producing hydrolyzate.

Now, the solvent-expelling step according to this invention will be described below. Specifically, since the esterification reaction is performed in a dehydrating solvent, the reaction solution resulting from the esterification reaction mentioned above is necessary to be distilled to expel the dehydrating solvent by evaporation. When the esterification reaction is performed in the presence of an acid catalyst, after the esterification step mentioned above, the resultant reaction solution is subjected to the partial neutralization step mentioned above to neutralize the acid catalyst and a part of the (meth)acrylic acid and subsequently distilled to expel the dehydrating solvent by evaporation.

Now, a preferred embodiment of the solvent-expelling step will be described below.

The present inventors have found that when a water-soluble polymerization inhibitor is added to the reaction solution in an amount of not more than 1000 ppm, preferably not more than 500 rpm, and more preferably not more than 300 ppm, and particularly preferably 0 ppm, based on the total amount of alcohol and (meth)acrylate as raw materials during the course of the expulsion by distillation of the dehydrating solvent from the reaction solution at the solvent-expelling step after the completion of the esterification reaction (optionally followed by the partial neutralization step), the water-soluble polymerization inhibitor which is added primarily for the purpose of inhibiting polymerization would quite unexpectedly induce polymerization of the unaltered raw materials, the esterified product, or the mixture thereof and give rise to a high-molecular weight substance because this polymerization inhibitor possesses polymerizing activity, through feebly, that the polymerization inhibitor added during the course of the esterification reaction can function effectively also during the course of the expulsion of the dehydrating agent by distillation, and that the occurrence of high-molecular weight substance can be prevented without using a water-soluble polymerization inhibitor at all. If the amount of the water-soluble polymerization inhibitor to be used exceeds 1000 ppm based on the total amount of alcohol and (meth) acrylic acid as raw materials, therefore, the polymerizing activity which is possessed by the water-soluble polymerizing inhibitor would induce occurrence of such a high-molecular weight substance as mentioned above. When the esterified product containing the high-molecular weight substance is utilized as a monomer component, the cement dispersant using the resultant polymer is at a disadvantage in being adversely affected by the high-molecular weight substance.

For the solvent-expelling step, since the esterification reaction is carried out in the presence of a polymerization inhibitor, when this polymerization inhibitor happens to be capable of functioning effectively after the esterification reaction (and also after the partial neutralization step) as mentioned above, the solution which is used during the solvent-expelling step does not need to be additionally supplemented with a polymerization inhibitor. When the partial neutralization is performed using an aqueous solution of alkali of low concentration, water is present in a comparatively large amount in the reaction solution. Exclusively when a polymerization inhibitor which has been used during the course of the esterification reaction is sparingly soluble or insoluble in water and does not function very effectively after the esterification reaction (and also after the partial neutralization), for example, since the unaltered raw materials and esterified product possibly dissolve in water and polymerize, it is commendable to add a water-soluble polymerization inhibitor in an amount in such a range as to manifest the polymerization-inhibiting ability more effectively than the polymerizing activity (the range specified above), in view of preventing the unaltered raw materials and esterified product possibly dissolve in water from polymerization and in view of the relation between the function of polymerization due to the polymerizing activity possessed by the water-soluble polymerization inhibitor and the polymerization inhibiting ability inherent therein, and then to heat the reaction solution to a temperature to be specified herein below to expel by distillation therefrom the dehydrating solvent in the form of an azeotropic mixture with water.

The water-soluble polymerization inhibitor which can be used herein is not particularly restricted. As concrete examples thereof, hydroquinone, methoquinone, catechol and the derivatives thereof (such as, for example, p-t-butyl catechol), and hydroquinone monomethyl ether may be cited. Among other examples cited above, hydroquinone and methoquinone are commendable because of comparative low polymerizing activity. These water-soluble polymerization inhibitors may be used either singly or in the form of a mixture of two or more members.

According to the second aspect, this invention is to provide a method for the production of a polycarboxylic acid type copolymer (referred to simply as "copolymer" or "polymer" in the present specification) for the used in a cement dispersant which comprises subjecting a polyalkylene glycol represented by the following formula (1) (simply referred to as "polyalkylene glycol" in the present specification);

$$R^1O(R^2O)_nH \tag{1}$$

wherein $R^1$ represents a hydrocarbon group of 1 to 30 carbon atoms, $R^2O$ represents an oxyalkylene group of 2 to 18 carbon atoms, providing that the repeating units, $R^2O$, may be the same or different and that when the $R^2O$'s are in the form of a mixture of two or more species, the repeating units, $R^2O$, may be added either in a block form or in a random form, and n represents an average addition mol number of oxyalkylene groups and is in the range of 1 to 300, to the esterification reaction with (meth)acrylic acid in a dehydrating solvent in the presence of an acid catalyst and a polymerization inhibitor at a reaction temperature of not higher than 130° C. at a solvent circulating speed of not less than 0.5 cycle/hour, to obtain an alkoxy polyalkylene glycol mono(meth)acrylic acid type monomer (a), copolymerizing 5 to 98% by weight of said alkoxy polyalkylene glycol mono(meth)acrylic acid type monomer (a), 95 to 2% by weight of a (meth)acrylic acid type monomer (b) represented by the following formula (2):

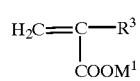

$$\tag{2}$$

wherein $R^3$ represents a hydrogen atom or a methyl group, and $M^1$ represents a hydrogen atom, a monovalent metal element, a divalent metal element, an ammonium group, or an organic amine group, and 0 to 50% by weight of a monomer (c) copolymerizable with the monomers mentioned above, providing that the total amount of the monomers (a), (b), and (c) be 100% by weight.

In the above aspect, the term "polyalkylene glycol" used therein is defined similarly to the term "alcohol" used in the first aspect, except for that n does not embrace 0. Then, such terms as "(meth)acrylic acid" and "esterification reaction" are as defined in the first aspect mentioned above.

Methods for the production of a polycarboxylic acid type copolymer (including the salts thereof; similarly applicable hereinafter) may not be particularly restricted so long as it can produce a polymer, depending on the intended use therefor, by adopting an alkoxy polyalkylene glycol mono (meth)acrylic acid type monomer as a monomer component and subjecting this monomer component to the polymerization. The method should be interpreted as embracing what is polymerized in conformity with the intended use. For example, a cement dispersant excelling in cement dispersing ability can be produced by subjecting an alkoxy polyalkylene glycol mono(meth)acrylic acid type monomer to the polymerization in combination with (meth)acrylic acid (or the salt thereof) and optionally a monomer copolymerizable with these monomer components by any of the known methods as disclosed in JP-B-59-18,338, JP-A-09-86,990, and JP-A-09-286,645. These methods, however, should not be exclusive examples. Naturally, the polymerization methods which are disclosed in the patent publications cited in the detailed description are applicable. Besides them, various polymerization methods heretofore known to the art can applied as a matter of course. The esterified product can find utility in other applications including a pigment dispersant for calcium carbonate, carbon black, ink, and other pigments, and a scale remover, a dispersant for a slurry of gypsum and water, a dispersant for CWM, a thickener, and etc. As concrete examples thereof, methods which produces a polymer using the esterified product according this invention instead of a polymer as disclosed in JP-A-09-211,968 and JP-A-10-10,047 may be cited, all of which are contained in the scope of this invention.

More specifically, the method for the production of a polycarbonic acid type copolymer according to this invention comprises subjecting an alkoxy polyalkylene glycol mono(meth)acrylic acid type monomer, a (meth)acrylic acid (salt) monomer, and optionally a monomer copolymerizable with such monomers to the polymerization.

Here, for the purpose of obtaining a polycarboxylic acid type copolymer as desired, it suffices to copolymerize an alkoxy polyalkylene glycol mono(meth)acrylic acid type monomer and other monomer components by the use of a polymerization initiator. This copolymerization can be carried out by such a method as by polymerization in a solvent, bulk polymerization, and etc.

The polymerization in a solvent can be performed batchwise or continuously. As concrete examples of the solvent which can be used in the polymerization, water; lower alcohols such as methyl alcohol, ethyl alcohol, and isopropyl alcohol; aromatic or aliphatic hydrocarbons such as benzene, toluene, xylene, cyclohxane, and n-hexane; ester compounds such as ethyl acetate; and ketone compounds such as acetone and methylethyl ketone may be cited. In terms of the solubility of the esterified product, i.e. the monomer component as a raw material, and the resultant copolymer and the convenience of the copolymer during use, it is prefrable to use at least one member selected from the group consisting of water and lower alcohols of 1 to 4 carbon atoms. In this case, among other lower alcohols of 1 to 4 carbon atoms, methyl alcohol, ethyl alcohol, and isopropyl alcohol may be used particularly effectively.

When the polymerization is performed in an aqueous medium, such water-soluble polymerization initiators as persulfates of ammonium or alkali metals or hydrogen peroxide maybe used for initiating the polymerization. In this case, the polymerization initiator may be used in combination with an accelerator such as, for example, sodium hydrogen sulfite or Mohr's salt. In the case of the polymerization using a lower alcohol, an aromatic hydrocarbon, an aliphatic hydrocarbon, an ester compound, or a ketone compound as a solvent, peroxides such as benzoyl peroxide and lauroyl peroxide; hydroperoxides such as cumene hydroperoxide; and aromatic azo compounds such as azobisisobutyronitrile may be used as a polymerization initiator. In this case, the polymerization initiator can be used in combination with an accelerator such as an amine compound. In the case of the polymerization using a mixed solvent of water with a lower alcohol, a polymerization initiator may be suitably selected among various polymerization initiators and various combinations of a polymerization initiator and an accelerator as mentioned above. The polymerization temperature may be generally in the range of 0° to 120° C., although it may be suitably selected depending on the kind of a solvent and a polymerization inhibitor to be used.

The bulk polymerization can be carried out using as a polymerization initiator a peroxide such as benzoyl peroxide or lauroyl peroxide; hydroperoxide such as cumene hydroperoxide; or an aliphatic azo compound such as azobisisobutyronitrile at a temperature in the range of 50° to 200° C.

For the adjustment of a molecular weight of the obtained polymer, it is permissible to use additionally a thiol type chain transfer agent. The thiol type chain transfer agent which can be used herein may be represented by the formula; HS-$R^5$-Eg (wherein $R^5$ represents an alkyl group of 1 to 2 carbon atoms, E represents a —OH, —$COOM^2$, —$COOR^6$, or —$SO_3M^2$ group, wherein $M^2$ represents a hydrogen atom, a monovalent metal element, a divalent metal element, an ammonium group, or an organic amine group, and $R^6$ represents an alkyl group of 1 to 10 carbon atoms, and g is an integer in the range of 1 to 2). As concrete examples thereof, mercaptoethanol, thioglycerol, thioglycolic acid, 2-mercaptopropionic acid, 3-mercaptopropionic acid, thiomalic acid, octyl thioglycolate, and octyl 3-mercapto propionate may be cited. These thiol type chain transfer agents may be used either singly or in the form of a mixture of two or more members.

The polymer which can be obtained as described above can be used in its unmodified form as a main component for varying end products such as a cement dispersant. Optionally, a polymer salt which is obtained by further neutralizing the polymer with an alkaline substance may be used as a main component for varying end products including a cement dispersant. As preferred concrete examples of the alkaline substance which is used for the neutralization, inorganic substances such as hydroxides, chlorides, and carbonates of monovalent metals and divalent metals; ammonia; and organic amines may be cited.

The alkoxy polyalkylene glycol mono(meth)acrylic acid type monomer components which can be used in the method for the production of a polymer according to this invention may be used either singly or in the form of two or more members. Especially when two or more such monomer components are used in a mixed form, it is commendable to use a suitably selected combination of two or more species differing in manifestation of characteristics so as to allow characteristics (including function and performance) to manifest conforming to the intended use. The combination of the following two species proves particularly advantageous.

As such analkoxypolyalkylene glycolmono(meth)acrylic acid type monomer, a mixture of a first esterified product ($a^1$) which has an average addition mol number, n, in the formula (1) in the range of 1 to 97, preferably in the range of 1 to 10 with a second esterified product ($a^2$) which has an average addition mol number, n, in the formula (1) in the range of 4 to 100, preferably in the range of 11 to 100, providing that the average addition mol number of the second esterified product ($a^2$) is not less than 3 larger than the average addition mol number of the first esterified product ($a^1$), is an advantageous combination.

The method for producing the mixture of the first esterified product ($a^1$) with the second esterified product ($a^2$) is as described for the method for the production of an esterified product as mentioned above. The production may be otherwise attained by separately producing these first and second esterified products ($a^1$) and ($a^2$) in accordance with the esterification reaction or by subjecting the mixture of relevant alcohols and (meth)acrylic acid respectively to the esterification reaction. Particularly, the latter method allows the production to be carried out inexpensively on a commercial scale.

In this case, the weight ratio of the first esterified product ($a^1$) to the second esterified product ($a^2$) is in the range of 5/95 to 95/5, preferably 10/90 to 90/10.

As concrete examples of the first esterified product ($a^1$), methoxy (poly)ethylene glycol mono(meth)acrylate, methoxy (poly)propylene glycol mono(meth)acrylate, methoxy (poly)butylene glycol mono(meth)acrylate, methoxy (poly) ethylene glycol (poly)propylene glycol mono(meth)acrylate, methoxy (poly)ethylene glycol (poly)butylene glycol mono (meth)acrylate, methoxy (poly)propylene glycol (poly) butylene glycol mono(meth)acrylate, methoxy (poly) ethylene glycol (poly)propylene glycol (poly)butylene glycol mono(meth)acrylate, ethoxy (poly)ethylene glycol mono(meth)acrylate, ethoxy (poly)propylene glycol mono (meth)acrylate, ethoxy (poly)butylene glycol mono(meth) acrylate, ethoxy (poly)ethylene glycol (poly)propylene glycol mono(meth)acrylate, ethoxy (poly)ethylene glycol (poly)butylene glycol mono(meth)acrylate, ethoxy (poly) propylene glycol (poly)butylene glycol mono(meth) acrylate, and ethoxy (poly)ethylene glycol (poly)prpopylene glycol (poly)butylene glycol mono(meth)acrylate may be cited. It is important that the first esterified product ($a^1$) should possess hydrophobicity in the short-chain alcohol of the side chain thereof.

From the viewpoint of easy copolymerization, the side chain preferably contains many ethylene glycol units. The esterified product ($a^1$), therefore, is preferably an alkoxy (poly)ethylene glycol mono(meth)acrylate having an average addition mol number in the range of 1 to 97, preferably 1 to 10.

As concrete examples of the second esterified product ($a^2$), methoxy polyethylene glycol mono(meth)acrylate, methoxy polyethylene glycol (poly)propylene glycol mono (meth)acrylate, methoxy polyethylene glycol (poly)butylene glycol mono(meth)acrylate, methoxy polyethylene glycol (poly)propylene glycol (poly)butylene glycol mono(meth) acrylate, ethoxy polyethylene glycol mono(meth)acrylate, ethoxy polyethylene glycol (poly)propylene glycol mono (meth)acrylate, ethoxy polyethylene glycol (poly)butylene glycol mono(meth)acrylate, and ethoxy polyethylene glycol (poly)propylene glycol (poly)butylene glycol mono(meth) acrylate may be cited.

To obtain a high water-reducing properties, it is important that cement particles should be dispersed by the steric repellency and hydrophilicity of an alcohol chain having an average addition mol number in the range of 4 to 100 in the second esterified product ($a^2$). For this purpose, the polyalkylene glycol chain is preferably incorporated therein many oxyethylene groups. Therefore, a polyethylene glycol chain is the most preferable. The average addition mol number of the alkylene glycol chain, n, in the second esterified product ($a^2$) may be in the range of 4 to 100, preferably 11 to 100.

As concrete examples of the (meth)acrylic acid (salt) monomer which can be used in the method for the production of the polymer of this invention, acrylic acid, methacrylic acid, and monovalent metal salts, divalent metal salts, ammonium salts, and organic amine salts of such acids may be cited. These (meth)acrylic acid (salt) monomers may be used either singly or in the form of a mixture of two or more members.

As concrete examples of the monomer copolymerizable with the monomer components, i.e., the esterified product monomer and the (meth)acrylic acid (salt) monomer which can be used in the method for the production of the polymer of this invention, dicarboxylic acids such as maleic acid, fumaric acid, citraconic acid, mesaconic acid, and itaconic acid; monoesters or diesters of these dicarboxylic acids with alcohols represented by the formula; $HO(R^{11}O)_rR^{12}$ (wherein $R^{11}O$ represents one species or a mixture of two or more species of oxyalkylene groups of 2 to 4 carbon atoms, providing that in the case of a mixture of two or more species, the oxyalkylene groups may be added in a block form or a random form, r represents an average addition mol number of the oxyalkylene group, and is an integer in the range of 1 to 100, and $R^{12}$ represents a hydrogen atom or an alkyl group of 1 to 22 carbon atoms, preferably 1 to 15 carbon atoms); unsaturated amides such as (meth) acrylamide and (meth)acryl alkyl amides; vinyl esters such as vinyl acetate and vinyl propionate; unsaturated sulfonic acids such as vinyl sulfonic acid, (meth)allyl sulfonic acid, sulfoethyl (meth)acrylate, 2-methyl propane sulfonic acid (meth)acrylamide, and styrene sulfonic acid, and the monovalent metal salts, divalent metal salts, ammonium salts, and organic amine salts thereof; aromatic vinyls such as styrene and .-methyl styrene; esters of phenyl group-containing alcohols such as aliphatic alcohols of 1 to 18, preferably 1 to 15 carbon atoms or benzyl alcohol with (meth)acrylic acid; polyalkylene glycol mono(meth) acrylates; and polyalkylene glycol mono(meth)ally ethers may be cited. These monomers may be used either singly or in the form of a mixture of two or more members.

The cement dispersant of this invention which has as a main component thereof the copolymer obtained as described above can manifest excellent cement-dispersing properties and slump-retaining properties.

The cement dispersant according this invention can incorporate therein at least one cement dispersant selected from the group consisting of naphthalene type cement dispersants, aminosulfonic acid type cement dispersants, polycarboxylic acid type cement dispersants, and lignin type cement dispersants which have been known to the art, in addition to the polymer component specified above. The cement dispersant according this invention may be formed solely of the polymer mentioned above or, when necessary, may incorporate therein various components mentioned above and to be shown herein below so as to acquire additional values. A composition of such additional components to be incorporated varies largely with the presence or absence of additive function aimed at. It cannot be specified uniquely but may be varied copiously from the mode of using the polymer wholly (100% by weight) or as a main component to the mode of adding the polymer component mentioned above as a high additive value component in a suitable amount to the conventional cement dispersant. The content of the polycarboxylic acid type copolymer in the cement dispersant according to this invention, however, may be generally in the range of 5 to 100% by weight, preferably in the range of 50 to 100% by weight, based on the total amount of all the components of the composition.

The cement dispersant according to this invention may additionally incorporate therein an air entraining agent, a cement wetting agent, an expanding agent, a water-proofing agent, a retarding agent, an accelerating agent, a water-soluble macromolecular substance, a thickener, a coagulating agent, a dry shrinkage allaying agent, a strength enhancer, a cure accelerator, and a defoaming agent besides conventional cement dispersants.

The cement dispersant having as a main component thereof the polymer obtained as described above can promote dispersion of cement by being incorporated in a cement composition which comprises at least cement and water.

The cement dispersant according to this invention can be used for such hydraulic cements as portland cement, Blite-rich cement, alumina cement, and various mixed cements or for hydraulic materials other than cements, such as gypsum.

Since the cement dispersant according to this invention have such actions and effects as described above, it can manifest outstanding effects even in a smaller amount as compared with a conventional cement dispersant. When this cement dispersant is used in mortar or concrete which uses hydraulic cement, for example, it suffices to add the cement dispersant thereto in an amount in the range of 0.001 to 5%, preferably 0.01 to 1%, based on the weight of cement. This addition brings various favorable effects such as accomplishing a high water-reducing ratio, enhancing slump loss preventing ability, decreasing an unit water content, exalting strength, and improving durability. If the added amount is less than 0.001%, the product would be deficient in performance. Conversely, if it exceeds 5%, the excess would bring no proportionate addition to the effect and consequently impair the economy of the use.

The cement dispersant according to this invention preferably contains as its main component a polymer having a specific weight average molecular weight and a specific difference obtained by subtracting a peak top molecular weight from a weight average molecular weight. In this case, the weight average molecular weight of the polycarboxylic acid type copolymer according to this invention may be decided suitably in the optimum range, depending on the kind of expected use, and set within the optimum range of 500 to 500000, preferably 5000 to 300000, in terms of polyethylene glycol determined by gel permeation chromatography. The difference obtained by subtracting the peak top molecular weight from the weight average molecular weight of the polymer must be in the range of 0 to 8000, preferably 0 to 7000. If the weight average molecular weight is less than 500, the shortage would be at a disadvantage in lowering the water-reducing properties of the cement dispersant. If this weight average molecular weight conversely exceeds 500000, the excess would be at a disadvantage in degrading the water-reducing properties and the slump loss preventing ability of the cement dispersant. If the different obtained by subtracting the peak top molecular weight from the weight average molecular weight exceeds 8000, the excess will be at a disadvantage in lowering the slump retaining ability of the produced cement dispersant.

According to the third aspect, this invention is to provide a method for the production of a polycarboxylic acid type copolymer which comprises subjecting p parts by weight of a polyalkylene glycol represented by the following formula (1):

$$R^1O(R^2O)_nH \qquad (1)$$

wherein $R^1$ represents a hydrocarbon group of 1 to 30 carbon atoms, $R^2O$ represents an oxyalkylene group of 2 to 18 carbon atoms, providing that the repeating units, $R^2O$, may be the same or different and that when the $R^2O$'s are in the form of a mixture of two or more species, the repeating units, $R^2O$, may be added either in a block form or in a random form, and n represents an average addition mol number of oxyalkylene groups and is in the range of 1 to 300, and q parts by weight of (meth)acrylic acid to the esterification reaction in a dehydrating solvent in the presence of an acid catalyst and a polymerization inhibitor at a reaction temperature of not higher than 130° C. at a solvent circulating speed of not less than 0.5 cycle/hour providing that p and q satisfy the relation of the following formula:

$$40 \geq [(p/n^{1/2})/q] \times 100 \geq 200$$

and then copolymerizing the resultant reaction mixture.

In the above aspect, the terms such as "polyalkylene glycol", "(meth)acrylic acid", and "esterification reaction" which are used in the second aspect described above have the same meanings, excepting the definition concerning the amount of polyalkylene glycol and (meth)acrylic acid to be used.

The third aspect described above is characterized by the fact that when the esterification reaction is carried out by allowing the (meth)acrylic acid to be present in an excess amount relative to the polyalkylene glycol, the alkoxy polyalkylene glycol mono(meth)acrylic acid type monomer consequently obtained exists in the form of a mixture containing (meth)acrylic acid and that the polycarboxylic acid type copolymer can be produced by subjecting this mixture in its unmodified form or optionally in combination with a (meth)acrylic acid (salt) monomer and a monomer copolymerizable with such monomers, preferably in its unmodified form, to the copolymerization. Since the production of the polycarboxylic acid type copolymer according to the third aspect permits omission of the step of isolating the alkoxy polyalkylene glycol mono(meth)acrylic acid, this method is suitable for the mass production and proves advantageous from the industrial point of view.

In the above aspect, it is essential that the amount, p parts by weight, of the polyalkylene glycol to be used and the amount, q parts by weight, of the (meth)acrylic acid to be used satisfy the relation of the following formula:

$$40 \geq [(p/n^{1/2})/q] \times 100 \geq 200$$

wherein n represents an average addition mol number of the oxyalkylene group, and is in the range of 1 to 300. In the present specification, the value caluculated by the formula: $40 \geq [(p/n^{1/2})/q] \times 100$, is referred to occasionally as "K value". The K value is a criterion for representing an average number of polyalkylene glycol chains per weight of the carboxylic acid. In this invention, the K value is preferred to be in the range of 42 to 190 ($42 \geq K$ value $\geq 190$), more preferably in the range of 45 to 160 ($45 \geq K$ value $\geq 160$). In this case, if the K value is less than 40, the cement dispersant consequently obtained would be deficient in cement-dispersing properties. Conversely, if the K value exceeds 200, the excess would be at a disadvantage in markedly increasing the reaction time of esterification and widely lowering the productivity, in addition to similarly degrading the cement-dispersing properties of the produced cement dispersant.

Now, this invention will be more specifically described below with reference to working examples. In the examples, the term "%" refers to "% by weight" and the term "part" to "part by weight" unless otherwise specified.

EXAMPLE 1

Figure 2:
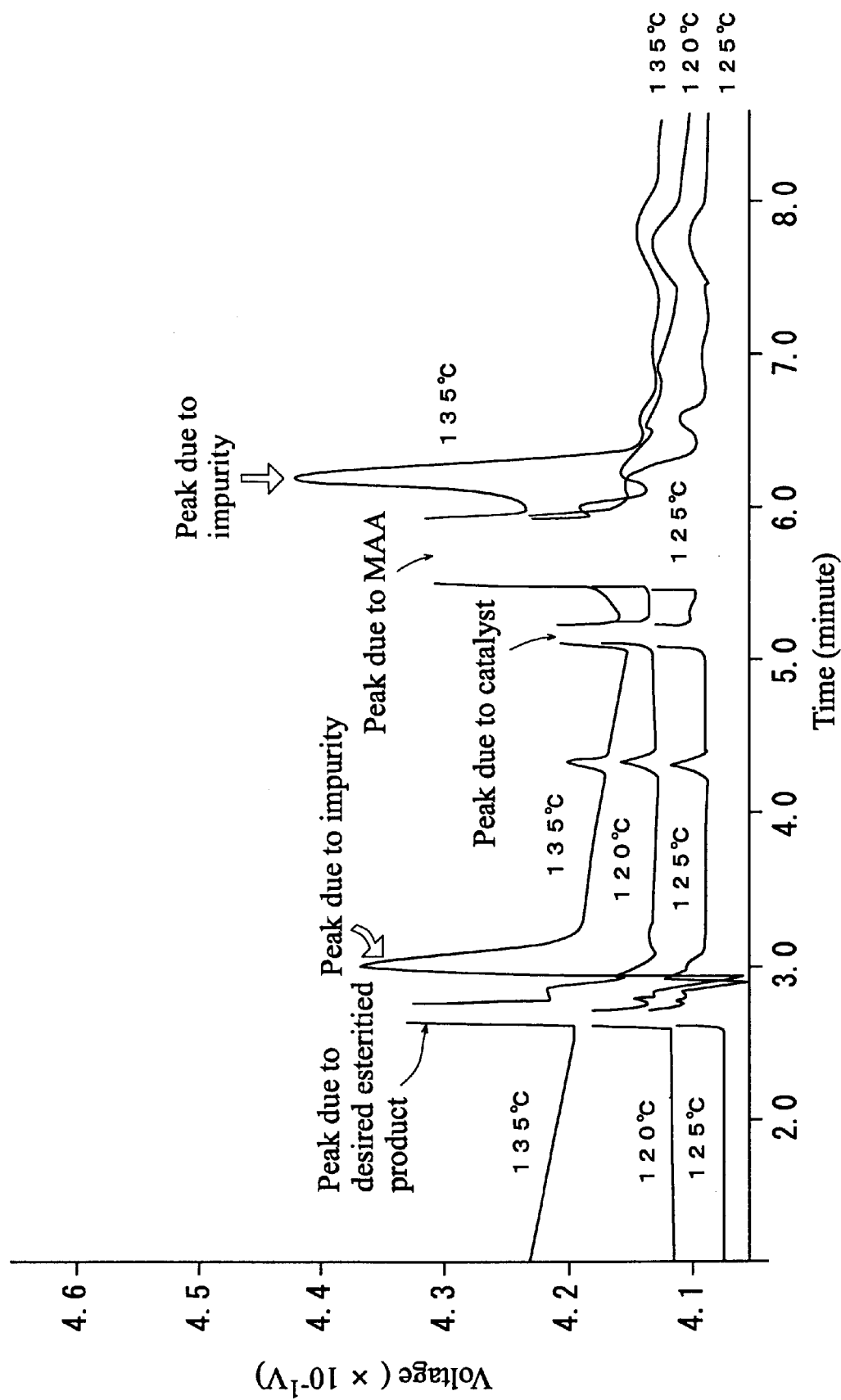
FIG. 2 is a diagram of a capillary electrophoresis chart showing the results of the determination, by means of capillary electrophoresis, of impurities contained in aqueous solutions of esterified products (1) and (2) and an aqueous solution of esterified product for comparison (1) obtained respectively in Examples 1 and 2 and in Control 1 using varying reaction temperatures.

In an externally jacketed glass reaction tank (30 liters in inner volume) provided with a thermometer, a stirrer, a separator of formed water, and a reflux condenser (condenser), 16500 parts of methoxy poly(n=25)ethylene glycol, 4740 parts (K value=70) of methacrylic acid, 235 parts of paratoluene sulfonic acid hydrate, 5 parts of phenothiazine, and 1060 parts of cyclohexane were placed. Then, the resultant mixture was subjected to the esterification reaction at a reaction temperature of 120° C. and, while the esterification reaction was in process, the flow volume (by volume) of the solvent to be refluxed was measured with a flow meter disposed on a path returned to the reaction tank from the circulation system composed of the separator of formed water and the reflux condenser and the temperature of the jacket on the reaction tank was set at 135° C. and, when necessary, suitably adjusted so that the solvent circulating speed was maintained at 5 cycles/hour. After the arrival of the ratio of esterification at 99% was confirmed in about 20 hours, 135 parts of an aqueous 49% sodium hydroxide solution and 4890 parts of water were added to the reaction solution to neutralize the paratoluene sulfonic acid. The neutralized reaction solution and 8 parts of hydroquinone added thereto were heated to expel the cyclohexane in the form of an azeotropic mixture with water. After the expulsion of the cyclohexane by distillation, adjusting water was added to the residue, to obtain an aqueous 80% esterified product solution (1). The resultant aqueous esterified product solution (1) was assayed by the capillary electrophoresis under the conditions indicated below to determine the content of impurities. The composition, the conditions, and the test results of the reaction in the present example are shown in Table 1 below and the capillary electrophoresis chart is shown in FIG. 2. The chart of FIG. 2 shows exclusively the peaks due to the esterified product aimed at, the catalyst (PTS), and the raw material (MAA) and shows no discernible peaks due to impurities. That is, the aqueous esterified product solution (1) contained no discernible impurities.

<Conditions of electrophoresis determination>

Instrument for measurement: Capillary chromatography made by Waters and sold under trademark designation of "Quanta 4000"

Column used: Column, 75 μm×60 cm, made by Waters and sold under trademark designation of "AccuSep-"Migration buffer used: 20millimoles/gof Sodiumborate Voltage: 20.00 KV

EXAMPLE 2

The esterification reaction was performed by following the procedure of Example 1 while changing the temperature of the jacket provided on the reaction tank to 140° C. and the reaction temperature to 125° C., respectively. After the arrival of the ratio of esterification at 100% was confirmed in about 18 hours, the treatment was made by following the procedure of Example 1 to obtain an aqueous 80% esterified product solution (2). The resultant aqueous esterified product solution (2) was assayed by the capillary electrophoresis in the same manner as in Example 1. The composition, the conditions, and the test results of the reaction in the present example are shown in Table 1 below and the capillary electrophoresis chart is shown in FIG. 2. The chart of FIG. 2 shows exclusively the peaks due to the esterified product aimed at, the catalyst (PTS), and the raw material (MAA) and shows no discernible peaks due to impurities. That is, the aqueous esterified product solution (2) contained no discernible impurities.

EXAMPLE 3

An aqueous 80% esterified product solution (3) was obtained by following the procedure of Example 1 while using as a reaction tank an externally jacketed SUS 316 reaction tank (30 m³ in inner volume) provided with a thermometer, a stirrer, a separator of formed water, and a shell-and-tube type condenser (comprising a shell of 750 mm in inside diameter and 4000 mm in length, and 485 tubes of 24 mm in inside diameter and having a heat transfer surface area of 150 m²). When the aqueous esterified product solution (3) was assayed by the capillary electrophoresis in the same manner as in Example 1, the chart exclusively shows the peaks due to the esterified product aimed at, the catalyst (PTS), and the raw material (MAA) and shows no peaks due to impurities. That is, the aqueous esterified product solution (3) thus obtained contained no discernible impurities.

EXAMPLE 4

An aqueous 80% esterified product solution (4) was obtained by following the procedure of Example 1 while using as a reaction tank an externally jacketed reaction tank to be lined with glass (30 m³ in inner volume) provided with a thermometer, a stirrer, a separator of formed water, and a shell-and-tube type condenser (comprising a shell of 750 mm in inside diameter and 4000 mm in length, and 485 tubes of 24 mm in inside diameter and having a heat transfer surface area of 150 m²). When the aqueous esterified product solution (4) was assayed by the capillary electrophoresis in the same manner as in Example 1, the chart exclusively shows the peaks due to the esterified product aimed at, the catalyst (PTS), and the raw material (MAA) and shows nopeaks due to impurities. That is, the aqueous esterified product solution (3) thus obtained contained no discernible impurities.

CONTROL 1

The esterification reaction was carried out by following the procedure of Example 1 while changing the temperature of the jacket provided on the reaction tank to 150° C. and the reaction temperature to 135° C., respectively. After the arrival of the ratio of esterification at 99% was confirmed in about 15 hours, an aqueous 80% esterified product solution for comparison (1) was obtained by following the procedure of Example 1. The aqueous esterified product solution for comparison (1) thus obtained was assayed by the capillary electrophoresis in the same manner as in Example 1. The composition, the conditions, and the test results of the reaction in the present control are shown in Table 1 below and the capillary electrophoresis chart is shown in FIG. 2. The chart of FIG. 2 shows a peak due to impurity at the position indicated by an open arrow in the diagram besides the peaks due to the esterified product aimed at, the catalyst (PTS), and the raw material (MAA). This fact demonstrates that the aqueous esterified product solution for comparison (1) contained impurities.

TABLE 1

| | Composition (Part by weight) | | | | | Conditions | | Results | |
|---|---|---|---|---|---|---|---|---|---|
| | Methoxy poly (n = 25) ethylene glycol | Methacrylic acid | Paratoluene sulfonic acid | Cyclo hexane | Pheno-thiazine | Reaction temperature (° C.) | Jacket temperature (° C.) | Esterification ratio (%)/ Reaction time (hr) | Impurity |
| Example 1 | 16500 | 4740 | 235 | 1060 | 5 | 120 | 135 | 99/20 | None |
| Example 2 | 16500 | 4740 | 235 | 1060 | 5 | 125 | 140 | 100/18 | None |
| Control 1 | 16500 | 4740 | 235 | 1060 | 5 | 135 | 150 | 99/15 | Present |

As shown in Table 1, the results of Examples 1 and 2 and Control 1 demonstrate that when the solvent circulating speed was substantially fixed and the reaction temperature was varied, impurities which are prone to degradation of cement-dispersing properties were formed as the reaction temperature rose above the upper limit specified by this invention, namely 130° C.

EXAMPLE 5

In an externally jacketed glass reaction tank (30 liters in inner volume) provided with a thermometer, a stirrer, a separator of formed water, and a reflux condenser (condenser), 2838 parts of methoxy poly(n=10)ethylene glycol, 1451 parts of acrylic acid, 48 parts of sulfuric acid, 2 parts of phenothiazine, and 1389 parts of cyclohexane were placed. Then, the resultant mixture was subjected to the esterification reaction at a reaction temperature of 80° C. and, while the esterification reaction was in process, the flow volume (by volume) of the solvent to be refluxed was measured with a flow meter disposed on a path returned to the reaction tank from the circulation system composed of the separator of formed water and the reflux condenser and the temperature of the jacket on the reaction tank was set at 135° C. and, when necessary, suitably adjusted so that the solvent circulating speed was maintained at 3 cycles/hour. After the arrival of the ratio of esterification at 100% was confirmed in about 5.5 hours, 92 parts of an aqueous 49% sodium hydroxide solution and 1000 parts of water were added to the reaction solution to neutralize the sulfuric acid. The neutralized reaction solution and 2 parts of hydroquinone added thereto were heated to expel the cyclohexane in the form of an azeotropic mixture with water. After the expulsion of the cyclohexane by distillation, adjusting water was added to the residue, to obtain an aqueous 80% esterified product solution (5). The composition, the conditions, and the test results of the reaction in the present example are shown in Table 2 below. The resultant aqueous esterified product solution (5) contained no discernible impurities.

EXAMPLE 6

The esterification reaction was carried out by following the procedure of Example 5 while the temperature of the jacket on the reaction tank was set at 110° C. so as to adjust the solvent circulating speed at 1 cycle/hour. After the arrival of the ratio of esterification at 100% was confirmed in about 8.5 hours, the treatment was performed in the same manner as in Example 5, to obtain an aqueous 80% esterified product solution (6). The composition, the conditions, and the test results of the reaction in the present example are shown in Table 2 below. The resultant aqueous esterified product solution (6) contained no discernible impurities.

EXAMPLE 7

An aqueous 80% esterified product solution (7) was obtained by following the procedure of Example 5 while using as a reaction tank an externally jacketed SUS 316 reaction tank (30 m$^3$ in inner volume) provided with a thermometer, a stirrer, a separator of formed water, and a shell-and-tube type condenser (comprising a shell of 750 mm in inside diameter and 4000 mm in length, and 485 tubes of 24 mm in inside diameter and having a heat transfer surface area of 150 m$^2$). When the aqueous esterified product solution (7) was assayed by the capillary electrophoresis in the same manner as in Example 1, the chart exclusively shows the peaks due to the esterified product aimed at, the catalyst (PTS), and the raw material (MAA) and shows no peaks due to impurities. That is, the aqueous esterified product solution (7) thus obtained contained no discernible impurities.

EXAMPLE 8

An aqueous 80% esterified product solution (8) was obtained by following the procedure of Example 5 while using as a reaction tank an externally jacketed reaction tank to be lined with glass (30 m$^3$ in inner volume) provided with a thermometer, a stirrer, a separator of formed water, and a shell-and-tube type condenser (comprising a shell of 750 mm in inside diameter and 4000 mm in length, and 485 tubes of 24 mm in inside diameter and having a heat transfer surface area of 150 m$^2$). When the aqueous esterified product solution (8) was assayed by the capillary electrophoresis in the same manner as in Example 1, the chart exclusively shows the peaks due to the esterified product aimed at, the catalyst (PTS), and the raw material (MAA) and shows nopeaks due to impurities. That is, the aqueous esterified product solution (8) thus obtained contained no discernible impurities.

CONTROL 2

The esterification reaction was carried out by following the procedure of Example 5 while the temperature of the jacket provided on the reaction tank was set at 90° C. so as to adjust the solvent circulating speed at 0.3 cycle/hour. After the arrival of the ratio of esterification at 100% was confirmed in about 11 hours, the treatment was performed in the same manner as in Example 5, to obtain an aqueous 80% esterified product solution for comparison (2). The composition, the conditions, and the test results of the reaction in this control are shown in Table 2 below. The aqueous esterified product solution for comparison (2) thus obtained contained no discernible impurities.

TABLE 2

| | Composition (Part by weight) | | | | | Conditions | | | Results | |
|---|---|---|---|---|---|---|---|---|---|---|
| | Methoxy poly (n = 10) ethylene glycol | Acrylic acid | Sulfuric acid | Cyclo hexane | Pheno- thiazine | Reaction Temp. (° C.) | Circulation speed of solvent (cycle/hr) | Jacket Temp. (° C.) | Reaction time (hr) | Esterification ratio (%) |
| Example 5 | 2838 | 1451 | 48 | 1389 | 2 | 80 | 3 | 135 | 5.5 | 100 |
| Example 6 | 2838 | 1451 | 48 | 1389 | 2 | 80 | 1 | 110 | 8.5 | 100 |
| Control 2 | 2838 | 1451 | 48 | 1389 | 2 | 80 | 0.3 | 90 | 11 | 100 |

As shown in Table 2, the results of Examples 5 and 6 and Control 2 demonstrate that when the reaction temperature was fixed and the solvent circulating speed was varied, a marked elongation of the reaction time was discerned as the solvent circulating speed fell below the lower limit specified by this invention.

EXAMPLE 9

The esterification reaction was carried out by following the procedure of Example 1 while changing the amount of paratoluene sulfonic acid hydrate added to 470 parts, and also changing the reaction temperature to 115° C. During the reaction, the formation of gel was not observed by visual inspection.

EXAMPLE 10

The esterification reaction was carried out by following the procedure of Example 9 while using as a reaction tank an externally jacketed SUS 316 reaction tank (30 m³ in inner volume) provided with a thermometer, a stirrer, a separator of formed water, and a shell-and-tube type condenser (comprising a shell of 750 mm in inside diameter and 4000 mm in length, and 485 tubes of 24 mm in inside diameter and having a heat transfer surface area of 150 m²). During the reaction, the formation of gel was not observed by visual inspection.

EXAMPLE 11

The esterification reaction was carried out by following the procedure of Example 9 while using as a reaction tank an externally jacketed reaction tank to be lined with glass (30 m³ in inner volume) provided with a thermometer, a stirrer, a separator of formed water, and a shell-and-tube type condenser (comprising a shell of 750 mm in inside diameter and 4000 mm in length, and 485 tubes of 24 mm in inside diameter and having a heat transfer surface area of 150 m²). During the reaction, the formation of gel was not observed by visual inspection.

EXAMPLE 12

The esterification reaction was carried out by following the procedure of Example 9 while changing the amount of the paratoluene sulfonic acid hydrate from 470 parts to 940 parts. During the reaction, the formation of gel was not observed by visual inspection.

EXAMPLE 13

The esterification reaction was carried out by following the procedure of Example 9 while using 707 parts of an aqueous 60% paratoluene sulfonic acid solution in place of 470 parts of paratoluene sulfonic acid hydrate. During the reaction, the formation of gel was not observed by visual inspection.

EXAMPLE 14

The esterification reaction was carried out by following the procedure of Example 9 while using 454 parts of an aqueous 70% paratoluene sulfonic acid solution in place of 470 parts of paratoluene sulfonic acid hydrate. During the reaction, the formation of gel was not observed by visual inspection.

EXAMPLE 15

The esterification reaction was carried out by following the procedure of Example 9 while using 606 parts of an aqueous 70% paratoluene sulfonic acid solution in place of 470 parts of paratoluene sulfonic acid hydrate. During the reaction, the formation of gel was not observed by visual inspection.

CONTROL 3

The esterification reaction was carried out by following the procedure of Example 9 while omitting the use of 470 parts by paratoluene sulfonic acid hydrate. During the reaction, the formation of gel in a large amount was observed by visual inspection.

EXAMPLE 16

The esterification reaction was carried out by following the procedure of Example 9 while changing the amount of the paratoluene sulfonic acid hydrate from 470 parts to 223 parts. During the reaction, the formation of gel in a small amount was observed by visual inspection.

EXAMPLE 17

The esterification reaction was carried out by following the procedure of Example 9 while using 848 parts of an aqueous 50% paratoluene sulfonic acid solution in place of 470 parts of paratoluene sulfonic acid hydrate. During the reaction, the formation of gel in a small amount was observed by visual inspection.

The compositions, the acid contents, X % by weight, and the water contents, Y % by weight, the values calculated by the formula: $1.81X-1.62$ to be preferably specified in this invention, the reaction temperatures, and the presence or absence of gel formation during the reaction which were found in the esterification reactions in Examples 9, 12 to 17 and Control 3 are shown in Table 3 below. FIG. 3 shows the relational expressions of $Y=1.81X-1.62$ and $Y=0$, and the correlation diagrams of X–Y obtained by plotting the (X, Y) coordinates in Examples 9, 12 to 17 and Control 3.

TABLE 3

| | Composition (Part by weight) | | | | | Ratio of acid content and water content in hydrate or aqueous solution of acid catalyst | | | | |
|---|---|---|---|---|---|---|---|---|---|---|
| | Methoxy poly (n = 25) ethylene glycol | Methacrylic acid | Hydrate or aqueous solution of paratoluene sulfonic acid | Cyclo hexane | Pheno- thiazine | Acid content X (wt. %) | Water content Y (wt. %) | 1.81 x −1.62 | Reaction Temp (° C.) | Gel Formation |
| Example 9 | 16500 | 4740 | Hydrate 470 | 1060 | 5 | 2 | 0.21 | 2 | 115 | None |
| Example 12 | 16500 | 4740 | Hydrate 940 | 1060 | 5 | 4 | 0.42 | 5.62 | 115 | None |
| Example 13 | 16500 | 4740 | 60% Aqueous solution 707 | 1060 | 6 | 2 | 1.33 | 2 | 115 | None |
| Example 14 | 16500 | 4740 | 70% Aqueous solution 454 | 1060 | 6 | 1.5 | 0.64 | 1.095 | 115 | None |
| Example 15 | 16500 | 4740 | 70% Aqueous | 1060 | 5 | 2 | 0.86 | 2 | 115 | None |

TABLE 3-continued

| | Composition (Part by weight) | | | | | Ratio of acid content and water content in hydrate or aqueous solution of acid catalyst | | | | |
|---|---|---|---|---|---|---|---|---|---|---|
| | Methoxy poly (n = 25) ethylene glycol | Methacrylic acid | Hydrate or aqueous solution of paratoluene sulfonic acid | Cyclo hexane | Pheno- thiazine | Acid content X (wt. %) | Water content Y (wt. %) | 1.81 × −1.62 | Reaction Temp (° C.) | Gel Formation |
| Example 16 | 16500 | 4740 | solution 606 Hydrate 223 | 1060 | 6 | 0.95 | 0.10 | 0.0995 | 115 | Small amount of gel |
| Example 17 | 16500 | 4740 | 50% Aqueous solution 848 | 1060 | 5 | 2 | 2.00 | 2.00 | 115 | Small amount of gel |
| Control 3 | 16500 | 4740 | None | 1060 | 5 | 0 | 0 | −1.62 | 115 | Large amount of gel |

Note) X and Y were calculated from the amount of paratoluene sulfonic acid hydrate used. (Since a molecular weight of paratoluene sulfonic acid is 172 and the hydrate is monohydrate, the calculation was carried out using the molecular weight of the hydrate of 190.)

EXAMPLE 18

In an externally jacketed glass reaction tank (30 liters in inner volume) provided with a thermometer, a stirrer, a separator of formed water, and a reflux condenser (condenser), 8200 parts of water was placed and, with the interior of the reaction tank replaced with nitrogen gas and kept stirred meanwhile, heated to 80° C. in an atmosphere of nitrogen. Then, to the reaction tank, a solution of 94 parts of 3-mercapto propionic acid in 13100 parts of the aqueous 80% esterified product solution (1) obtained in Example 1 was added dropwise over a period of four hours, and at the same time, a solution of 125 parts of ammonium persulfate in 1000 parts of water was added dropwise over a period of five hours. After the dropwise addition was completed, the resultant reaction mixture was left standing at 80° C. for one hour. Then, by further adjusting this reaction mixture with sodium hydroxide to a pH value of 8, polycarboxylic acid (1) of this invention was found to have a weight average molecular weight of 21000, in terms of polyethylene glycol determined by gel permeation chromatography.

By using the polycarboxylic acid (1) obtained as described above in its unmodified form as a cement dispersant, a cement composition (1) was prepared in accordance with the method for mortar test and tested for flow value. The results are shown in Table 4 below.

<Method for mortar test>

A cement composition (1) was prepared by kneading 240 parts of water containing the cement dispersant [polycarboxylic acid (1)] obtained as described above, 400 parts of ordinary portland cement (made by Taiheiyo Cement) as a cement, and 800 parts of standard sand produced at Toyoura by the use of a mortar mixer. The amount of the cement dispersant added is shown in Table 4 below.

Then, this cement composition (1) was placed to fill a hollow cylinder, 55 mm in diameter and 55 mm in height. The cylinder was gently raised vertically to allow the cement composition (1) to spread. The major diameter and the minor diameter of the spread cement composition (1) and the average thereof was reported as a flow value.

EXAMPLE 19

The esterification reaction was carried out by following the procedure of Example 1 while changing the amount of the methoxy poly(n=25)ethylene glycol to be used to 19430 parts and the amount of methacrylic acid to be used to 1810 parts (K value=215). After the arrival of the ratio of esterification at about 99% was confirmed in about 90 hours, 104 parts of an aqueous 49% sodium hydroxide solution and 4900 parts of water were added to the esterified product to neutralize the paratoluene sulfonic acid. The resultant product and 8 parts of hydroquinone added thereto were heated to expel the cyclohexane in the form of an azeotropic mixture with water. After the expulsion of the cyclohexane by distillation, adjusting water was added to the residue, to obtain an aqueous 80% esterified product solution (9).

In an externally jacketed glass reaction tank (30 liters in inner volume) provided with a thermometer, a stirrer, a separator of formed water, and a reflux condenser (condenser), 8200 parts of water was placed and, with the interior of the reaction tank replaced with nitrogen gas and kept stirred meanwhile, heated to 80° C. in an atmosphere of nitrogen. Then, a solution of 58 parts of 3-mercapto propionic acid in 13700 parts of the aqueous 80% esterified product solution (9) obtained as described above was added dropwise over a period of four hours, and at the same time, a solution of 122 parts of ammonium persulfate in 2300 parts of water was added dropwise over a period of five hours. After the dropwise addition was completed, the resultant reaction mixture was left standing at 80° C. for one hour. Then, by further adjusting this reaction mixture with sodium hydroxide to a pH value of 8, polycarboxylic acid (2) was found to have a weight average molecular weight of 19700, in terms of polyethylene glycol determined by gel permeation chromatography.

By using the polycarboxylic acid (2) obtained as described above in its unmodified form as a cement dispersant, a cement composition (2) was prepared in accordance with the method for mortar test and tested for flow value in the same manner as in Example 18. The results are shown in Table 4 below.

TABLE 4

| | Cement dispersant | Amount added[a] | Flow Value |
|---|---|---|---|
| Example 18 | Polycarboxylic acid (1) | 0.15% | 105 mm |
| Example 19 | Polycarboxylic acid (2) | 1.0% | 60 mm |

[a]Solid content as a reduced mass of cement (% by weight)

It is clearly noted from the results shown in Table 4 that the flow value markedly fell and consequently the cement-dispersing ability was decreased when the K value surpassed the upper limit specified in claim 9 of this invention.

The entire disclosure of Japanese Patent Application Nos. 10-268122 and 10-328687 filed on Sep. 22, 1998 and Nov. 18, 1998, respectively, including specification, claims, drawings and summary are incorporated herein by reference in its entirety.

What is claimed is:

1. A method for the production of an esterified product which comprises esterifying an alcohol represented by the following formula (1):

$$R^1O(R^2O)_nH \qquad (1)$$

wherein $R^1$ represents a hydrocarbon group of 1 to 30 carbon atoms, $R^2O$ represents an oxyalkylene group of 2 to 18 carbon atoms, providing that the repeating units, $R^2O$, may be the same or different and that when the $R^2O$'s are in the form of a mixture of two or more species, the repeating units, $R^2O$, may be added either in a block form or in a random form, and n represents an average addition mol number of oxyalkylene groups and is in the range of 0 to 300, with (meth)acrylic acid in a dehydrating solvent in the presence of an acid catalyst and a polymerization inhibitor, wherein a reaction temperature during the esterification reaction is not higher than 130° C. and a circulation speed of the solvent during the esterification reaction is not less than 0.5 cycle/hour.

2. A method according to claim 1, wherein said acid catalyst is used in the form of a hydrate and/or an aqueous solution and the amount of said acid catalyst to be used satisfies the relation of the following formula:

$$0<Y<1.81X-1.62$$

wherein X (% by weight) represents the weight ratio of the acid in the acid catalyst to the total weight of the alcohol and the (meth)acrylic acid as raw materials and Y (% by weight) represents the weight ratio of the water present in the hydrate and/or the aqueous solution of the acid catalyst to the total weight of the alcohol and the (meth)acrylic acid as raw materials.

3. A method according to claim 1, wherein said acid catalyst is a hydrate and/or an aqueous solution of paratoluene sulfonic acid.

4. A method according to claim 1, wherein said acid catalyst has a boiling point of not less than 150° C.

5. A method according to claim 4, wherein said acid catalyst is at least one member selected from the group consisting of paratoluene sulfonic acid, paratoluene sulfonic acid hydrate, sulfuric acid, and methane sulfonic acid.

6. A method according to claim 1, wherein said polymerization inhibitor is at least one member selected from the group consisting of phenothiazine, methoquinone, and hydroquinone.

7. A method according to according to claim 1, wherein in the formula (1), n represents an average addition mol number of an oxyalkylene group and is in the range of 2 to 300.

8. A method for the production of a polycarboxylic acid copolymer for the use in a cement dispersant which comprises subjecting a polyalkylene glycol represented by the following formula (1):

$$R^1O(R^2O)_nH \qquad (1)$$

wherein $R^1$ represents a hydrocarbon group of 1 to 30 carbon atoms, $R^2O$ represents an oxyalkylene group of 2 to 18 carbon atoms, providing that the repeating units, $R^2O$, may be the same or different and that when the $R^2O$'s are in the form of a mixture of two or more species, the repeating units, $R^2O$, may be added either in a block form or in a random form, and n represents an average addition mol number of oxyalkylene groups and is in the range of 1 to 300, to the esterification reaction with (meth) acrylic acid in a dehydrating solvent in the presence of an acid catalyst and a polymerization inhibitor at a reaction temperature of not higher than 130° C. at a solvent circulating speed of not less than 0.5 cycle/hour, to obtain an alkoxy polyalkylene glycol mono(meth)acrylic acid monomer (a), and copolymerizing 5 to 98% by weight of said alkoxy polyalkylene glycol mono (meth) acrylic acid monomer (a), 95 to 2% by weight of a (meth) acrylic acid monomer (b) represented by the following formula (2):

$$\begin{array}{c} H_2C{=}C{-}R^3 \\ COOM^1 \end{array} \qquad (2)$$

wherein $R^3$ represents a hydrogen atom or a methyl group, and $M^1$ represents a hydrogen atom, a monovalent metal element, a divalent metal element, an ammonium group, or an organic amine group, and 0 to 50% by weight of a monomer (c) copolymerizable with the monomers mentioned above, providing that the total amount of the monomers (a), (b), and (c) be 100% by weight.

9. A method for the production of a polycarboxylic acid copolymer for the use in a cement dispersant which comprises subjecting p parts by weight of a polyalkylene glycol represented by the following formula (1):

$$R^1O(R^2O)_nH \qquad (1)$$

wherein $R^1$ represents a hydrocarbon group of 1 to 30 carbon atoms, $R^2O$ represents an oxyalkylene group of 2 to 18 carbon atoms, providing that the repeating units, $R^2O$, may be the same or different and that when the $R^2O$'s are in the form of a mixture of two or more species, the repeating units, $R^2O$, may be added either in a block form or in a random form, and n represents an average addition mol number of oxyalkylene groups and is in the range of 1 to 300, and q parts by weight of (meth)acrylic acid to the esterification reaction in a dehydrating solvent in the presence of an acid catalyst and a polymerization inhibitor at a reaction temperature of not higher than 130° C. at a solvent circulating speed of not less than 0.5 cycle/hour providing that p and q satisfy the relation of the following formula:

$$40 \geq [(p/n^{1/2})/q] \times 100 \geq 200$$

and then copolymerizing the resultant reaction mixture.

* * * * *